(12) United States Patent
Ganpath et al.

(10) Patent No.: US 8,945,199 B2
(45) Date of Patent: Feb. 3, 2015

(54) SEALING APPARATUS AND METHODS OF USE

(75) Inventors: Raj P. Ganpath, Mountain View, CA (US); Amy Lee, Sunnyvale, CA (US); Craig Rosenberg, Palo Alto, CA (US); Sherwin Llamido, Newark, CA (US); Steven L. Herbowy, Palo Alto, CA (US); Michael A. Evans, Palo Alto, CA (US); Thomas A. Howell, Palo Alto, CA (US); Charles S. Taylor, Stockton, NJ (US); K. T. Venkateswara Rao, San Jose, CA (US)

(73) Assignee: Nellix, Inc., Irvine, CA (US)

( * ) Notice: Subject to any disclaimer, the term of this patent is extended or adjusted under 35 U.S.C. 154(b) by 1096 days.

(21) Appl. No.: 12/478,225

(22) Filed: Jun. 4, 2009

(65) Prior Publication Data
US 2009/0318949 A1    Dec. 24, 2009

Related U.S. Application Data

(60) Provisional application No. 61/058,810, filed on Jun. 4, 2008.

(51) Int. Cl.
*A61F 2/06* (2013.01)
*A61F 2/07* (2013.01)
(Continued)

(52) U.S. Cl.
CPC ... *A61F 2/07* (2013.01); *A61F 2/95* (2013.01); *A61F 2/954* (2013.01);
(Continued)

(58) Field of Classification Search
CPC ............ A61F 2002/823; A61F 2002/077; A61F 2250/0003; A61F 2002/826; A61B 17/12113; A61B 2017/22054

USPC .............. 623/1.11, 1.25; 606/194–195
See application file for complete search history.

(56) References Cited

U.S. PATENT DOCUMENTS

| | | | |
|---|---|---|---|
| 4,565,738 A | 1/1986 | Purdy | |
| 4,638,803 A | 1/1987 | Rand | |

(Continued)

FOREIGN PATENT DOCUMENTS

| | | |
|---|---|---|
| DE | 4010975 A1 | 10/1991 |
| EP | 95302708.3 | 11/1995 |

(Continued)

OTHER PUBLICATIONS

Gilling-Smith, "Stent Graft Migration After Endovascular Aneurysm Repair," presented at 25th International Charing Cross Symposium, Apr. 13, 2003 [Power Point Presentation and Transcript], 56 pages total.

(Continued)

*Primary Examiner* — Darwin Erezo
*Assistant Examiner* — Martin T Ton
(74) *Attorney, Agent, or Firm* — Kilpatrick Townsend & Stockton, LLP; Kenneth R. Shurtz, Esq.

(57) ABSTRACT

A system for treating an aneurysm comprises at least a first double-walled filling structure having an outer wall and an inner wall and the filling structure is adapted to be filled with a hardenable fluid filling medium so that the outer wall conforms to the inside surface of the aneurysm and the inner surface forms a generally tubular lumen to provide blood flow. The first filling structure comprises a sealing feature which forms a fluid seal between the filling structure and the aneurysm or an adjacent endograft when the filling structure is filled with the hardenable fluid filling medium, thereby minimizing or preventing blood flow downstream of the seal.

22 Claims, 31 Drawing Sheets

(51) Int. Cl.
    *A61F 2/95*            (2013.01)
    *A61F 2/954*          (2013.01)
    *A61F 2/90*            (2013.01)

(52) U.S. Cl.
    CPC .... *A61F 2002/065* (2013.01); *A61F 2002/077* (2013.01); *A61F 2250/0003* (2013.01); *A61F 2250/0069* (2013.01); *A61F 2/90* (2013.01)
    USPC .......................................................... 623/1.11

(56) References Cited

U.S. PATENT DOCUMENTS

| | | | |
|---|---|---|---|
| 4,641,653 A | 2/1987 | Rockey | |
| 4,704,126 A | 11/1987 | Baswell | |
| 4,710,192 A | 12/1987 | Liotta | |
| 4,728,328 A | 3/1988 | Hughes et al. | |
| 4,731,073 A | 3/1988 | Robinson | |
| 4,733,665 A | 3/1988 | Palmaz | |
| 4,743,258 A | 5/1988 | Ikada | |
| 4,763,654 A * | 8/1988 | Jang | 606/195 |
| 4,856,516 A | 8/1989 | Hillstead | |
| 4,858,264 A | 8/1989 | Reinhart | |
| 4,892,544 A | 1/1990 | Frisch | |
| 4,936,057 A | 6/1990 | Rhoades | |
| 4,976,692 A | 12/1990 | Atad | |
| 5,002,532 A | 3/1991 | Gaiser | |
| 5,074,845 A | 12/1991 | Miraki | |
| 5,104,404 A | 4/1992 | Wolff | |
| 5,108,417 A | 4/1992 | Sawyer | |
| 5,122,154 A | 6/1992 | Rhodes | |
| 5,133,732 A | 7/1992 | Wiktor | |
| 5,139,480 A | 8/1992 | Hickle | |
| 5,156,620 A | 10/1992 | Pigott | |
| 5,195,984 A | 3/1993 | Schatz | |
| 5,199,226 A | 4/1993 | Rose | |
| 5,217,484 A | 6/1993 | Marks | |
| 5,222,970 A | 6/1993 | Reeves | |
| 5,234,437 A | 8/1993 | Sepetka | |
| 5,242,399 A | 9/1993 | Lau | |
| 5,250,071 A | 10/1993 | Palermo | |
| 5,261,916 A | 11/1993 | Engelson | |
| 5,263,964 A | 11/1993 | Purdy | |
| 5,292,331 A | 3/1994 | Boneau | |
| 5,314,444 A | 5/1994 | Gianturco | |
| 5,316,023 A | 5/1994 | Palmaz et al. | |
| 5,330,520 A | 7/1994 | Maddison et al. | |
| 5,330,528 A * | 7/1994 | Lazim | 623/1.25 |
| 5,334,217 A | 8/1994 | Das | |
| 5,350,397 A | 9/1994 | Palermo | |
| 5,352,199 A | 10/1994 | Tower | |
| 5,375,612 A | 12/1994 | Cottenceau | |
| 5,383,892 A | 1/1995 | Cardon | |
| 5,421,955 A | 6/1995 | Lau | |
| 5,423,849 A | 6/1995 | Engelson | |
| 5,425,739 A | 6/1995 | Jessen | |
| 5,425,744 A | 6/1995 | Fagan | |
| 5,441,510 A | 8/1995 | Simpson | |
| 5,441,515 A | 8/1995 | Khosravi | |
| 5,443,477 A | 8/1995 | Marin | |
| 5,443,496 A | 8/1995 | Schwartz | |
| 5,449,373 A | 9/1995 | Pinchasik | |
| 5,485,667 A | 1/1996 | Kleshinski | |
| 5,494,029 A | 2/1996 | Lane | |
| 5,496,277 A | 3/1996 | Termin | |
| 5,507,767 A | 4/1996 | Maeda | |
| 5,507,769 A | 4/1996 | Marin et al. | |
| 5,507,771 A | 4/1996 | Gianturco | |
| 5,514,115 A | 5/1996 | Frantzen | |
| 5,514,154 A | 5/1996 | Lau | |
| 5,522,882 A | 6/1996 | Gaterud | |
| 5,530,528 A | 6/1996 | Houki et al. | |
| 5,531,741 A | 7/1996 | Barbacci | |
| 5,534,024 A | 7/1996 | Rogers et al. | |
| 5,545,210 A | 8/1996 | Hess | |
| 5,549,662 A | 8/1996 | Fordenbacher | |
| 5,549,663 A | 8/1996 | Cottone, Jr. | |
| 5,554,181 A | 9/1996 | Das | |
| 5,562,641 A | 10/1996 | Flomenblit | |
| 5,562,698 A | 10/1996 | Parker | |
| 5,562,728 A | 10/1996 | Lazarus | |
| 5,569,295 A | 10/1996 | Lam | |
| 5,578,074 A | 11/1996 | Mirigian | |
| 5,578,149 A | 11/1996 | De Scheerder | |
| 5,591,195 A | 1/1997 | Taheri | |
| 5,591,223 A | 1/1997 | Lock | |
| 5,591,226 A | 1/1997 | Trerotola | |
| 5,591,228 A | 1/1997 | Edoga | |
| 5,591,230 A | 1/1997 | Horn | |
| 5,593,417 A | 1/1997 | Rhodes | |
| 5,601,600 A | 2/1997 | Ton | |
| 5,603,721 A | 2/1997 | Lau | |
| 5,605,530 A | 2/1997 | Fischell | |
| 5,607,442 A | 3/1997 | Fischell | |
| 5,607,445 A | 3/1997 | Summers | |
| 5,607,468 A | 3/1997 | Rogers | |
| 5,609,605 A | 3/1997 | Marshall | |
| 5,617,878 A | 4/1997 | Taheri | |
| 5,618,299 A | 4/1997 | Khosravi | |
| 5,624,411 A | 4/1997 | Tuch | |
| 5,630,840 A | 5/1997 | Mayer | |
| 5,632,760 A | 5/1997 | Sheiban | |
| 5,632,762 A | 5/1997 | Myler | |
| 5,632,763 A | 5/1997 | Glastra | |
| 5,632,771 A | 5/1997 | Boatman | |
| D380,266 S | 6/1997 | Boatman | |
| 5,634,941 A | 6/1997 | Winston | |
| 5,636,641 A | 6/1997 | Fariabi | |
| D380,831 S | 7/1997 | Kavteladze | |
| 5,662,614 A | 9/1997 | Edoga | |
| 5,665,117 A | 9/1997 | Rhodes | |
| 5,674,241 A | 10/1997 | Bley | |
| 5,676,697 A | 10/1997 | McDonald | |
| 5,683,449 A | 11/1997 | Marcade | |
| 5,690,643 A | 11/1997 | WiJay | |
| 5,693,038 A | 12/1997 | Suzuki et al. | |
| 5,693,067 A | 12/1997 | Purdy | |
| 5,693,088 A | 12/1997 | Lazarus | |
| 5,697,971 A | 12/1997 | Fischell | |
| 5,709,707 A | 1/1998 | Lock | |
| 5,718,713 A | 2/1998 | Frantzen | |
| 5,723,004 A | 3/1998 | Dereume | |
| 5,725,568 A | 3/1998 | Hastings | |
| 5,725,572 A | 3/1998 | Lam | |
| 5,728,068 A | 3/1998 | Leone | |
| 5,728,131 A | 3/1998 | Frantzen | |
| 5,728,158 A | 3/1998 | Lau | |
| 5,733,303 A | 3/1998 | Israel et al. | |
| 5,735,892 A | 4/1998 | Myers | |
| 5,735,893 A | 4/1998 | Lau | |
| 5,741,327 A | 4/1998 | Frantzen | |
| 5,741,333 A | 4/1998 | Frid | |
| 5,746,691 A | 5/1998 | Frantzen | |
| 5,755,769 A | 5/1998 | Richard | |
| 5,755,773 A | 5/1998 | Evans et al. | |
| 5,755,778 A | 5/1998 | Kleshinski | |
| 5,766,151 A | 6/1998 | Valley et al. | |
| 5,766,238 A | 6/1998 | Lau | |
| 5,769,882 A | 6/1998 | Fogarty et al. | |
| 5,776,114 A | 7/1998 | Frantzen | |
| 5,776,161 A | 7/1998 | Globerman | |
| 5,782,907 A | 7/1998 | Frantzen | |
| 5,785,679 A | 7/1998 | Abolfathi et al. | |
| 5,788,626 A | 8/1998 | Thompson | |
| 5,797,953 A | 8/1998 | Tekulve | |
| 5,800,393 A | 9/1998 | Sahota | |
| 5,800,512 A | 9/1998 | Lentz et al. | |
| 5,800,514 A | 9/1998 | Nunez | |
| 5,800,525 A | 9/1998 | Bachinski | |
| 5,807,404 A | 9/1998 | Richter | |
| 5,810,872 A | 9/1998 | Kanesaka | |
| 5,824,036 A | 10/1998 | Lauterjung | |
| 5,824,037 A | 10/1998 | Fogarty et al. | |
| 5,824,040 A | 10/1998 | Cox | |
| 5,824,049 A | 10/1998 | Ragheb | |

(56) References Cited

U.S. PATENT DOCUMENTS

| | | |
|---|---|---|
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula et al. |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman et al. |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Duerig et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 * | 9/2001 | Solovay et al. ............... 623/1.16 |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 7,022,100 B1 | 4/2006 | Aboul-Hosn et al. |
| 7,105,012 B2 * | 9/2006 | Trout, III ................... 623/1.11 |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | Depalma et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,951,448 B2 | 5/2011 | Lee et al. |
| 2001/0020184 A1 | 9/2001 | Dehdashtian et al. |
| 2001/0027337 A1 | 10/2001 | Di Caprio |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |

(56) References Cited

U.S. PATENT DOCUMENTS

| | | |
|---|---|---|
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov |
| 2003/0220649 A1 | 11/2003 | Bao et al. |
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1* | 5/2004 | Bell et al. .............. 424/489 |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1 | 4/2006 | Vardi et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1* | 7/2006 | Seguin .............. 623/1.23 |
| 2006/0184109 A1 | 8/2006 | Gobel |
| 2006/0206197 A1 | 9/2006 | Morsi |
| 2006/0212112 A1* | 9/2006 | Evans et al. .............. 623/1.25 |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162106 A1 | 7/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0198267 A1 | 8/2009 | Evans et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |

FOREIGN PATENT DOCUMENTS

| | | |
|---|---|---|
| EP | 1325717 | 7/2003 |
| EP | 1903985 | 4/2008 |
| FR | 2834199 A1 | 4/2003 |
| JP | 4-322665 A | 11/1992 |
| JP | 2003-525692 | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/19653 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 | 9/2000 |
| WO | WO 01/21108 | 3/2001 |
| WO | 01/66038 | 9/2001 |
| WO | 02/078569 A2 | 10/2002 |
| WO | 02/083038 A2 | 10/2002 |
| WO | WO 02/102282 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | 2004/004603 A1 | 1/2004 |
| WO | 2004/026183 A2 | 4/2004 |
| WO | 2004/026183 A3 | 4/2004 |
| WO | 2004/037116 A2 | 5/2004 |
| WO | 2004/037116 A3 | 5/2004 |
| WO | 2004/045393 A2 | 6/2004 |
| WO | 2006/012567 A2 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Carmi et al., "Endovascular stent-graft adapted to the endoluminal environment: prototype of a new endoluminal approach," J Endovasc Ther. Jun. 2002;9(3):380-381.

International Search Report and Written Opinion of PCT Application No. PCT/US2009/046310, dated Jul. 29, 2009, 9 pages total.

U.S. Appl. No. 61/052,059, filed May 9, 2008; first named inventor: Gwendolyn A. Watanabe.

Examination Report of corresponding Japanese Application No. 2011-512667, dated Jun. 18, 2013.

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

Journal of Endovascular Therapy; Apr. 2000; pp. 111, 114, 132-140; vol. 7' No. 2; International Society of Endovascular Specialists; Phoenix, AZ.

Donayre et al., "Fillable Endovascular Aneurysm Repair," Endovascular Today, pp. 64-66, Jan. 2009.

International Search Report of PCT/US 06/16403, dated Aug. 7, 2007. 2 pages.

International Search Report and Written Opinion of PCT Application No. PCT/US2006/062257, mailed Jan. 18, 2008. 7 pages total.

International Search Report and Written Opinion of PCT Application No. PCT/US07/69671, dated Jul. 7, 2008, 9 pages.

International Search Report and Written Opinion of PCT Application No. PCT/US09/34136, D dated Apr. 8, 2009, 16 pages total.

U.S. Appl. No. 12/371,087, filed Feb. 13, 2009, first named inventor: K.T. Venkateswara Rao.

International Search Report and Written Opinion of PCT Application No. PCT/US09/41718, dated Jun. 22, 2009, 23 pages total.

Supplementary European Search Report and Search Opinion of EP Patent Application No. 05773726, mailed Apr. 23, 2010, 6 pages total.

(56) References Cited

OTHER PUBLICATIONS

International Search Report and The Written Opinion of the International Searching Authority, Issued in PCT/US2012/032612 on Jul. 25, 2012, 13 pages.
The International Search Report of the International Searching Authority for Application No. PCT/US2012/021878, mailed on May 23, 2012, 4 pages.
The Written Opinion, including the search, of the International Searching Authority for Application No. PCT/US2012/021878, mailed May 23, 2012, 9 pages.
Extended European search report of corresponding EP Application No. 06751879.5, dated Apr. 16, 2013. 9 pages.
European Search Report and Search Opinion of EP Patent Application No. 06774540.6, mailed Mar. 30, 2010, 6 pages total.
EP report, dated Nov. 7, 2013, of corresponding EP Application No. 09733719.0.
Search report dated Oct. 17, 2013 of corresponding PCT/US2012/032612.
International Preliminary Report on Patentability PCT/US2012/021878 dated Aug. 1, 2013.
Report of European Patent Application No. 06850439.8 dated May 15, 2013.
Report for European Patent Application No. 06850439.8, dated Aug. 8, 2012.
Examination report for JP Application. No. 2008-547709 dated Dec. 13, 2011.
International Search Report and Written Opinion of PCT Application No. PCT /US2009/046308, mailed Nov. 17, 2009, 12 pages total.
International Preliminary Report on Patentability and Written Opinion of the International Searching Authority, Issued in PCT/US2010/061621 on Jul. 12,2012, 7 pages.
PCT International Search Report and Written Opinion dated Feb. 28, 2011 for PCT Application No. PCT/US2010/61621. 11 pages.
U.S. Appl. No. 60/855,889, filed Oct. 31, 2006; first named inventor: Steven L. Herbowy.
U.S. Appl. No. 12/429,474, filed Apr. 24, 2009; first named inventor: Steven L. Herbowy.

William Tanski, Mark Fillinger. *Outcomes of original and low-permeability Gore Excluder endoprosthesis for endovascular abdominal aortic aneurysm repair*. Journal of Vascular Surgery. Feb. 2007. p. 243-249.
Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.
Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.
Examination report of EP Application No. 06751879.5, dated Mar. 24, 2014. 5 pages.
Examination Report of Japanese Patent Application No. 2007-522822, dated Feb. 8, 2011.
Examination Report of Japanese Patent Application No. 2011-506487, dated Jun. 11, 2013.
Official Action for Japanese Patent Application No. 2008-547709; dated Oct. 30, 2012.
Examination Report of Japanese Patent Application No. 2008-547709, dated Jul. 22, 2013.
Examination Report of European Patent Application 03754880.7; dated Dec. 16, 2010.
Examination Report of European Patent Application 03754880.7; dated Dec. 22, 2011.
Examination Report of European App. 03754880.7, dated Feb. 22, 2013.
Examination Report of European Application No. 03754880.7; dated Jun. 29, 2012. 4 pages.
Extended European Search Report of Application No. 11180827.5, dated Jan. 30, 2012. 6 pages.
Search report of corresponding PCT/US2014/021928, mailed May 20, 2014. 8 pages.
Examination Report of Japanese Patent Application No. 2011-506487, dated May 7, 2014.

\* cited by examiner

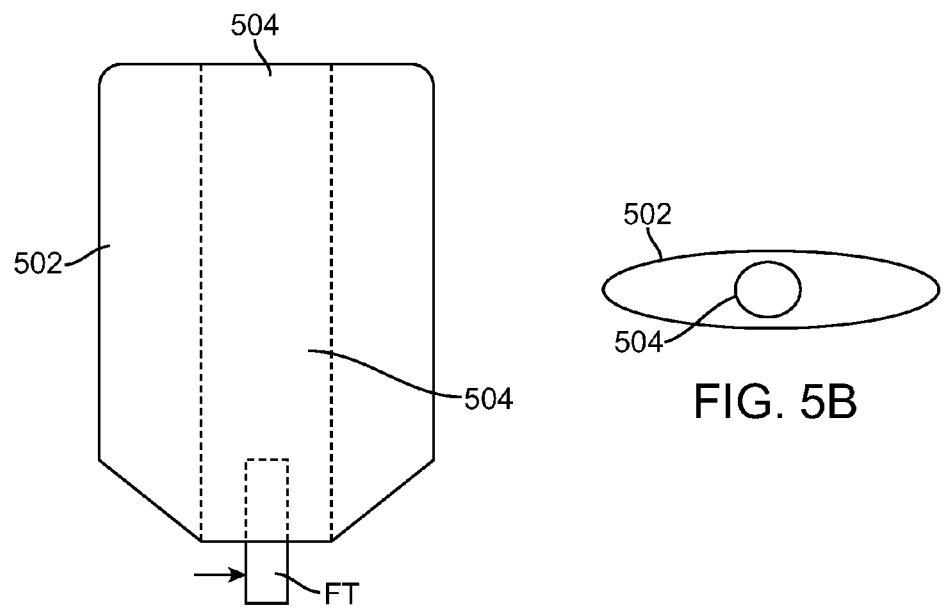
FIG. 5A
FIG. 5B
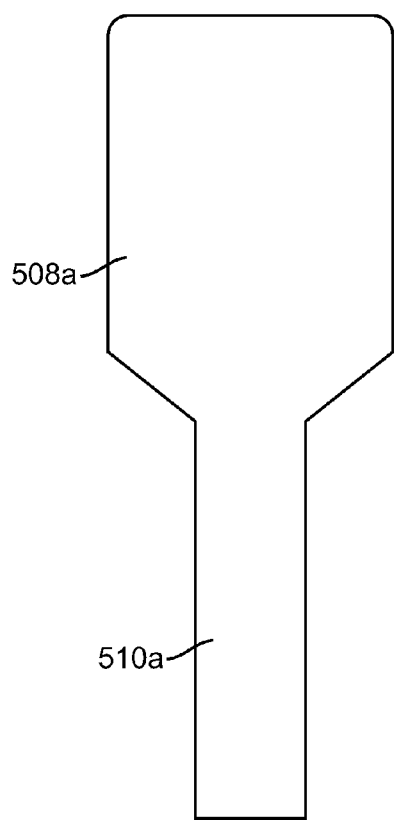
FIG. 5C
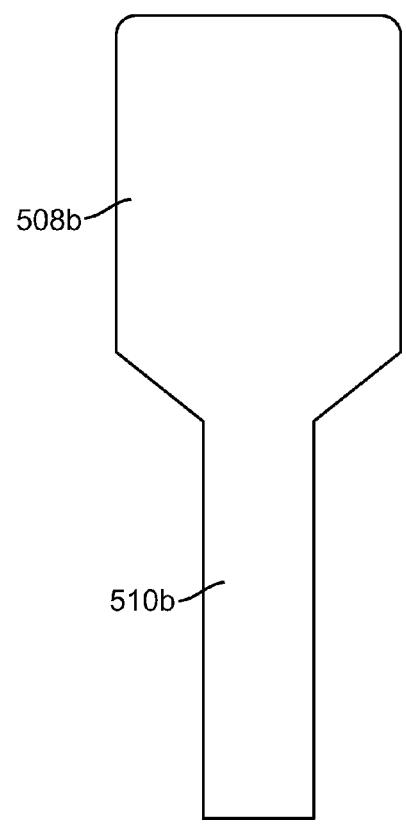
FIG. 5D

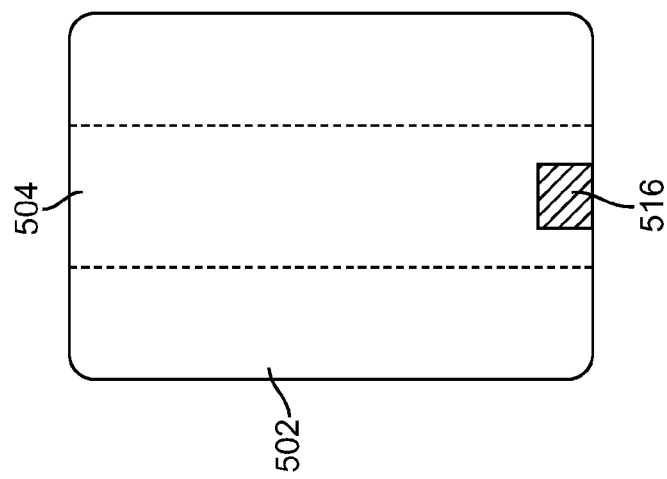
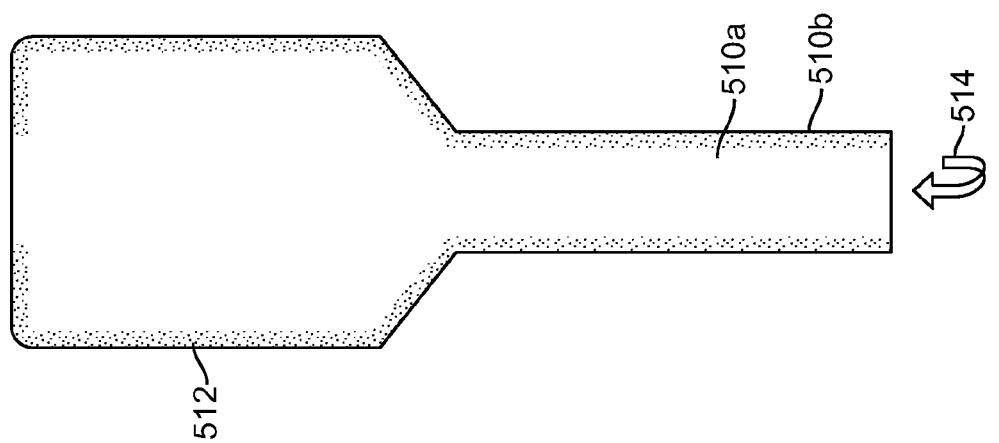

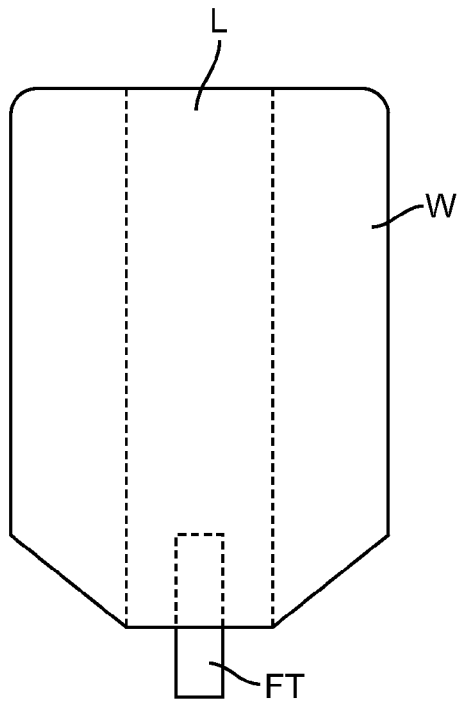
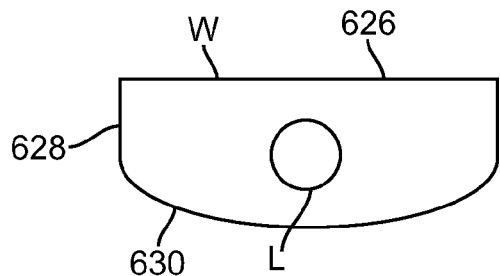
FIG. 8B
FIG. 8A
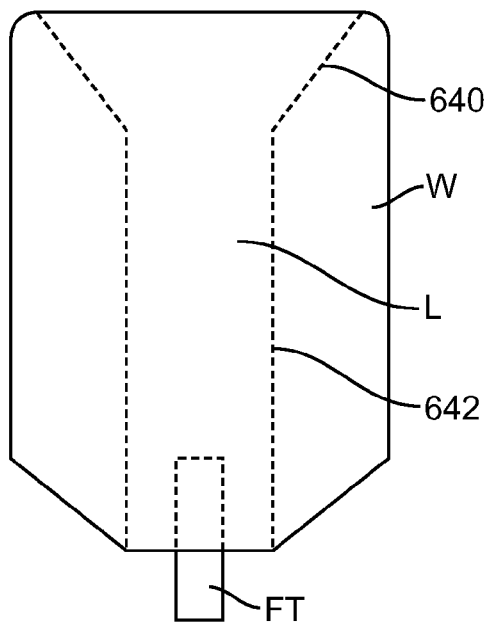
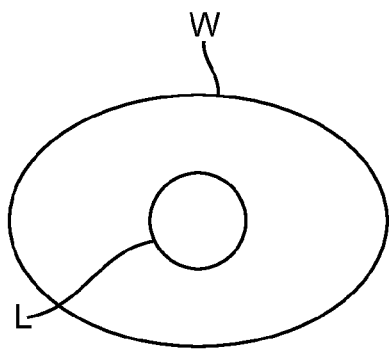
FIG. 9B
FIG. 9A

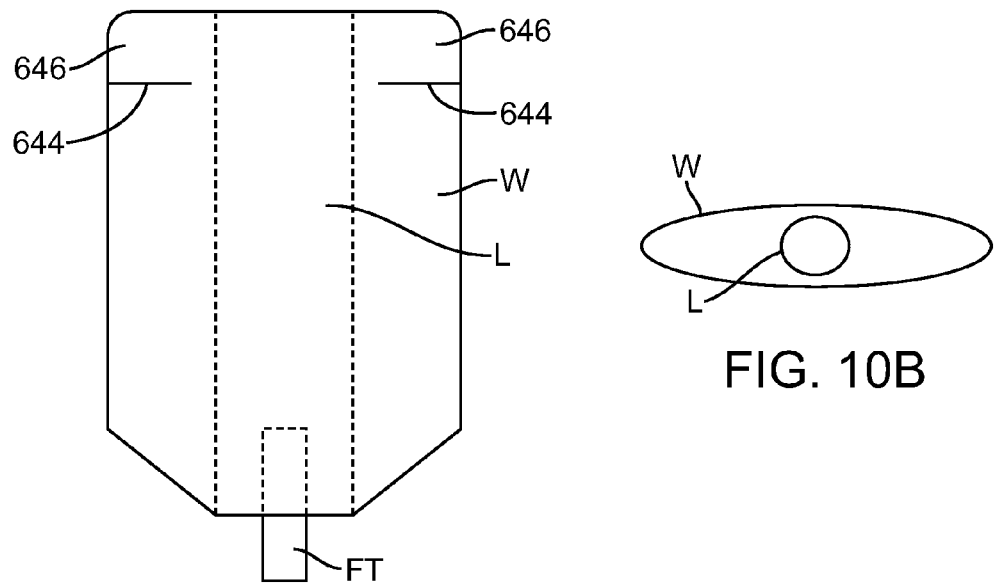
FIG. 10A
FIG. 10B
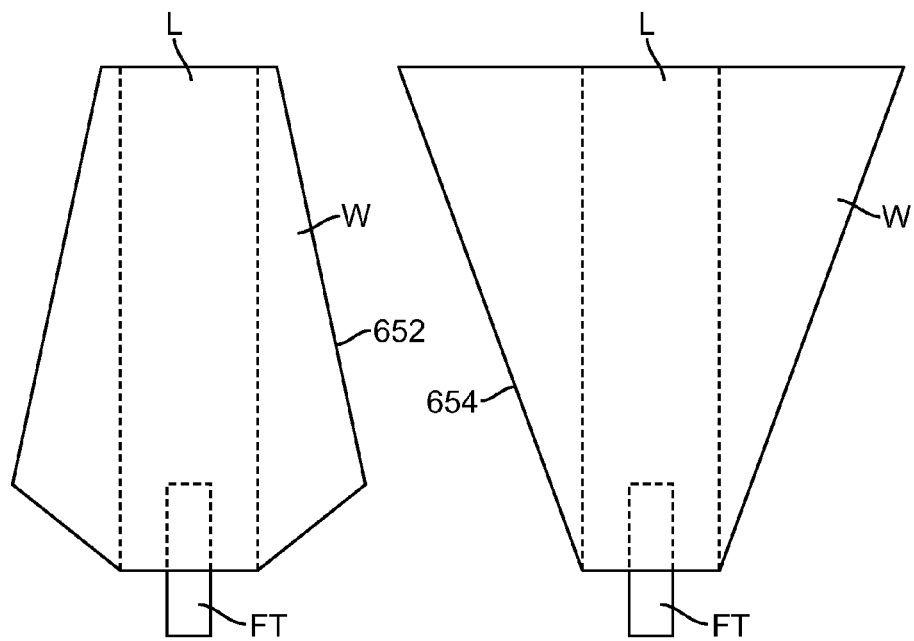
FIG. 11

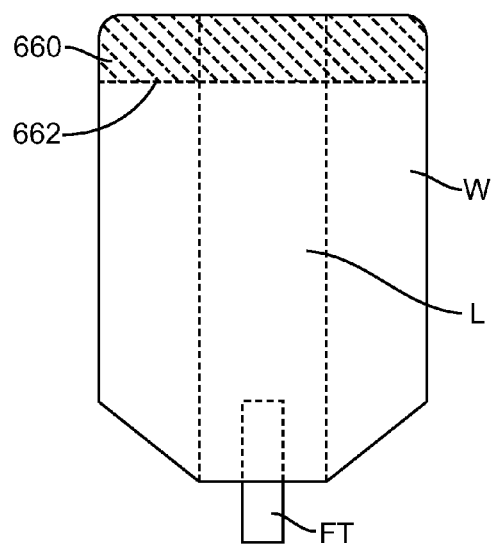
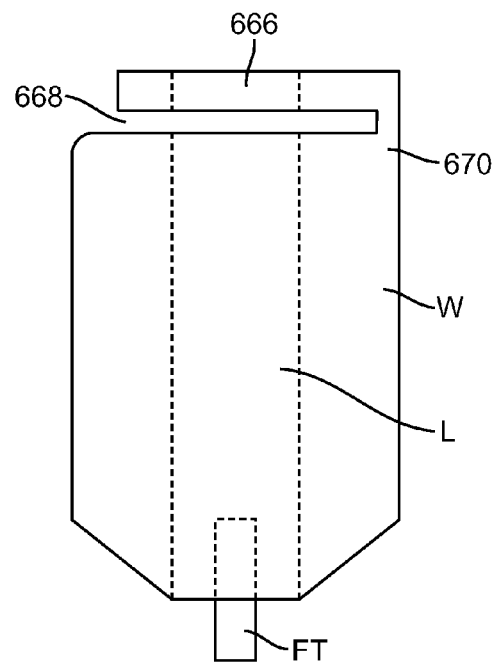
FIG. 12  FIG. 13
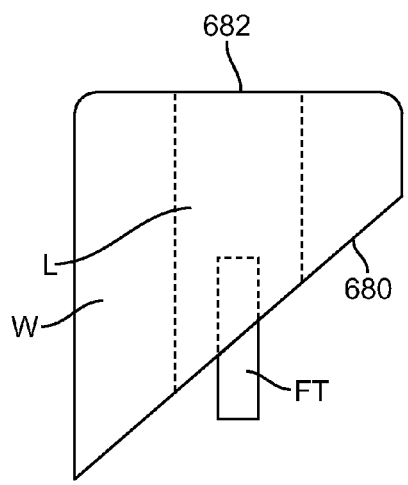
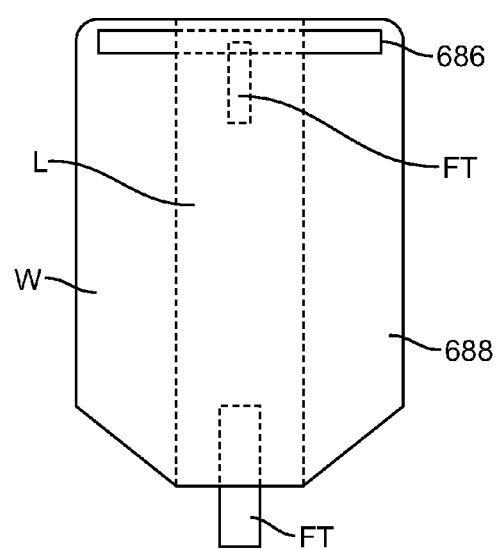
FIG. 14  FIG. 15

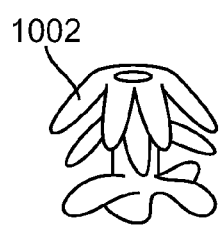
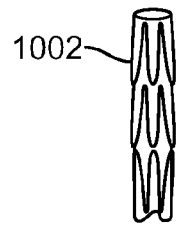
FIG. 33A    FIG. 33B
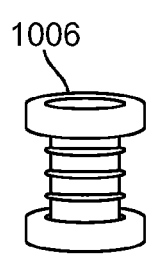
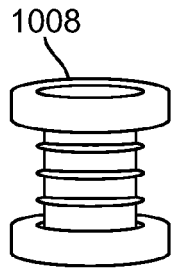
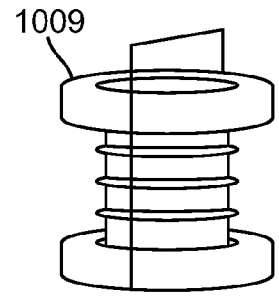
FIG. 34A
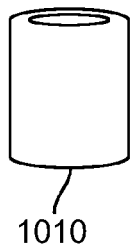
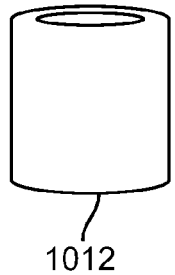
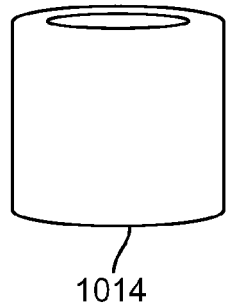
FIG. 34B
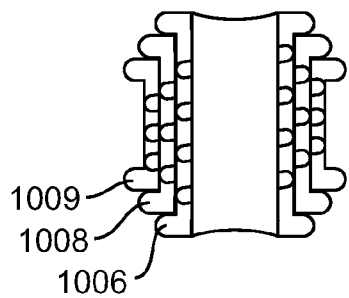
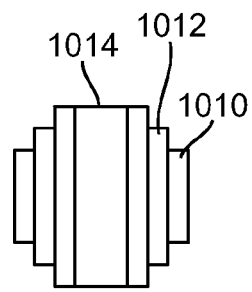
FIG. 34C    FIG. 34D

SEALING APPARATUS AND METHODS OF USE

CROSS-REFERENCES TO RELATED APPLICATIONS

The present application is a non-provisional of, and claims the benefit of priority under 35 U.S.C. §119(e) of U.S. Provisional Application No. 61/058,810 filed Jun. 4, 2008, the entire contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention relates generally to medical systems and methods for treatment. More particularly, the present invention relates to apparatus and methods for treating aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

The present invention is particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about eighty percent (80%) of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures may be problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. For example, a significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are often those who are not considered to be good surgical candidates.

Further shortcomings of the present endoluminal graft systems relate to both deployment and configuration. For example, many of the commercially available endovascular systems are too large (above 12 F) for percutaneous introduction. Moreover, current devices often have an annular support frame that is stiff and difficult to deliver as well as unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

In order to overcome some of the aforementioned challenges, the use of endograft systems having a scaffold structure and a filling structure has been proposed, such as in U.S. patent application Ser. No. 11/413,460 filed Apr. 28, 2006, the entire contents of which are incorporated herein by reference. These systems utilize a filling structure to help seal off and fill the aneurismal sac while creating a lumen for blood to traverse the aneurysm. Several references disclosing filling structures and which are the subject of the commonly owned, copending applications are described below. These systems may also include a stent-like scaffold which helps support the filling structure thereby further defining the lumen for blood flow. The filling structure may require a pre-filling step to help unfurl the filling structure prior to filling it with the hardenable filling material and an expandable balloon often is used to help support the endograft during filling and during hardening in order to ensure proper formation of a lumen for blood flow. Because the filling material may take some time to harden, the expanded balloon can occlude flow for an undesirable time. Additionally, even after filling and hardening of filling material in the filling structure, the aneurismal sac may not be completely sealed off and blood can still flow into the sac. For these reasons it would be desirable to provide alternative apparatus and methods that create a better seal between the aneurismal sac and the endograft. It would also be desirable to provide apparatus and methods that help filling structures expand and conform to the aneurysm anatomy. Moreover, it would also be desirable for sealing apparatus and methods to minimize or eliminate the need for a separate unfurling step as well as minimizing the need to use an inflated balloon for support during filling and hardening that can obstruct blood flow. It would also be desirable that the alternative apparatus have a low profile for ease of delivery and percutaneous introduction as well as flexibility to allow advancement of the device through torturous vessels such as the iliac arteries. It would further be desirable that such devices can accommodate a variety of different vessel and aneurysm anatomies. At least some of these objectives will be met by the inventions described hereinbelow.

2. Description of the Background Art

U.S. Patent Publication No. 2006/0025853 describes a double-walled filling structure for treating aortic and other aneurysms. Copending, commonly owned U.S. Patent Publication No. 2006/0212112, describes the use of liners and extenders to anchor and seal such double-walled filling structures within the aorta. The full disclosures of both these publications are incorporated herein by reference. PCT Publication No. WO 01/21108 describes expandable implants attached to a central graft for filling aortic aneurysms. See also U.S. Pat. Nos. 5,330,528; 5,534,024; 5,843,160; 6,168,592; 6,190,402; 6,312,462; 6,312,463; U.S. Patent Publications 2002/0045848; 2003/0014075; 2004/0204755; 2005/0004660; and PCT Publication No. WO 02/102282.

BRIEF SUMMARY OF THE INVENTION

The present invention provides apparatus and methods for the treatment of aneurysms, particularly aortic aneurysms including both abdominal aortic aneurysms (AAA) and thoracic aortic aneurysms (TAA).

In a first aspect of the present invention, a system for treating an aneurysm comprises at least a first double-walled filling structure having an outer wall and an inner wall and the filling structure is adapted to be filled with a hardenable fluid filling medium so that the outer wall conforms to the inside surface of the aneurysm and the inner surface forms a generally tubular lumen to provide blood flow. The first filling structure comprises a sealing feature which forms a fluid seal between the filling structure and the aneurysm or an adjacent endograft when the filling structure is filled with the hardenable fluid filling medium. This minimizes or prevents blood flow downstream of the seal.

The walls of the filling structure may comprise ePTFE and the seal may be disposed upstream of the aneurysm, for example in the aneurysm neck. Sometimes the walls of the filling structure may be coated with another polymer such as polyurethane. The tubular lumen may have a substantially circular cross-section and the first filling structure may comprise an elliptical cross-section when the filling structure is filled with the hardenable filling medium. The edges of the first filling structure may be sealed together so that the filling structure can withstand a filling pressure of up to 300 mm Hg above a patient's normal systolic blood pressure without bursting. Some systems may also comprise a thrombogenic material such as polyurethane, polycarbonate, polyester, ePTFE, polyolefin, parylene, gelatin and silicone. The thrombogenic material may be coupled with an outer surface of the first filling structure and it may be formed into one of sutures, felts, velours, weaves, knits, hydrogels, foams, coils, sheets and combinations thereof. The thrombogenic material may also comprise a thrombogenic drug.

In some embodiments the first filling structure may include a main body having a main body width and the sealing feature may comprise a narrow neck region that is coupled with the main body. The narrow neck region may have a width that is less than the main body width. The width of the narrow neck region may be approximately 2% to approximately 20% of the main body width. Sometimes the sealing feature may include a flat shoulder on an upper portion of the filling structure. Other embodiments may have a sealing feature which includes a tapered shoulder region on an upper portion of the filling structure.

Still, in other embodiments the first filling structure may comprise an upper layer of material having an upper layer width and a lower layer of material having a lower layer width that is wider than the upper layer width. The upper and lower layers are fixedly coupled together so as to form the sealing feature which comprises a substantially flat upper outer surface and an arcuate lower outer surface when the first filling structure is filled with hardenable filling medium. The first filling structure may comprise a D-shaped cross-section when filled with hardenable filling medium.

The sealing feature may comprise a tapered region in the tubular lumen with the taper disposed near an upper portion of the first filling structure. The tapered region may flare inwardly from the upper portion of the first filling structure to a lower portion of the first filling structure. In other embodiments, the first filling structure may comprise an upper layer of material and a lower layer of material, wherein at least a portion of the upper layer is fixedly coupled with at least a portion of the lower layer of material which forms the sealing feature. In this case, the sealing feature comprises an upper filling region and a lower filling region formed by the seal with the two filling regions in fluid communication with one another. The upper filling region may hold a smaller volume of filling medium than the lower filling region and the seal may be formed along a line. The line may extend from an outer edge of the first filling structure inward towards the tubular lumen.

In other embodiments, the system may further comprise a second double-walled filling structure having an outer wall and an inner wall, wherein the second filling structure is adapted to be filled with a hardenable fluid filling medium so that the outer wall conforms to the inside surface of the aneurysm and the inner surface forms a generally tubular lumen to provide blood flow. The second filling structure may comprise a sealing feature which forms a fluid seal between the filling structure and the aneurysm or an adjacent endograft when the second filling structure is filled with the hardenable fluid filling medium. This minimizes or prevents blood flow downstream of the seal. The sealing feature of the first double-walled filling structure may comprise an outer surface having a first shape and the sealing feature of the second double-walled filling structure may comprise an outer surface having a second shape. The first and second shapes may be complementary to one another. In some embodiments, the first and second shapes comprise complementary tapers.

In still other embodiments, the sealing feature may comprise a foam filled region of the first filling structure and the foam filled region may be discrete from the remainder of the first filling structure. The discrete foam filled region may be fluidly isolated from the region filled with the hardenable filling medium. In other embodiments, the sealing feature may comprise an arm in fluid communication with the region filled with the hardenable filling medium. Alternatively, the sealing feature may comprise a slot that is substantially transverse to a longitudinal axis of the first double-walled filling structure. The slot may at least partially bisect the first double-walled filling structure into two fillable sections. The foam may be substituted for any other material that provides the desired compliance to the foam filled region, such as gels, suture material, etc.

Some embodiments may have a sealing feature which comprises a winged region that flares radially outward from the first double-walled filling structure. The winged region may comprise a tapered shoulder on an outer surface of the first double-walled filling structure. The sealing feature may further comprise a tapered lower region in the tubular lumen which flares radially outward from an upper part to a lower part of the first filling structure. Sometimes the sealing feature may also comprise a restraining element that is disposed at least partially around the tubular lumen. The restraining element may be adapted to restrict radial expansion of the tubular lumen to a predetermined size or shape. Sometimes the restraining element comprises a band extending circumferentially around the tubular lumen.

The sealing feature may comprise an enlarged head region and a tapered lower region on the first filling structure. The tapered region flares radially outward as the distance from the head region increases. The sealing feature may comprise a lower tubular cuff region coupled with the first filling structure and a winged portion on the first filling structure. The sealing feature may also include an upper tubular cuff region coupled with the first filling structure. Sometimes the sealing feature includes a skeletal frame disposed in between the inner and outer walls of the first filling structure and the inner wall radially expands inward as the first filling structure is filled with hardenable filling material. Alternatively, the first filling structure may be disposed on the inside surface of a radially expandable scaffold and the sealing feature may comprise a portion of the inner wall that is adapted to radially expand inward to engage and seal against an adjacent endograft.

The sealing feature may comprise an angled bottom edge on the first filling structure. In some embodiments, the filling structure may comprise a straight top edge and the angled bottom edge forms an acute angle relative to the top edge. In other embodiments, the sealing feature comprises a discrete filling compartment separate from the filling space of the first double-walled filling structure and fluidly uncoupled thereto. The discrete filling compartment may have a rectangular shaped region and the hardenable filling medium may surround the discrete filling compartment. An elongate flexible filling tube may be slidably engaged with the discrete filling compartment and the filling space.

In other embodiments, the sealing feature may comprise a shoulder that is disposed on a lower portion of the first filling structure. The first filling structure may have a main body width and the shoulder may have a shoulder width that is less than the main body width. The sealing feature may comprise an undercut region in the first filling structure that is adapted to expand outwardly when the first filling structure is filled with hardenable filling material.

The sealing feature may include a plurality of filaments coupled with the first filling structure and extending axially therefrom. These filaments may include a thrombogenic material. The thrombogenic material may also be a cape that is disposed at least partially over the first filling structure and coupled thereto. The sealing feature could also be a thrombogenic annular ring that is disposed at least partially around the first filling structure. Other sealing features may include a plurality of flanges that are coupled with the first filling structure. The flanges may have a width that progressively decreases relative to an adjacent flange. Also, the flanges may have a thickness that progressively decreases relative to an adjacent flange.

In still other embodiments the sealing feature may comprise a skeletal frame that is coupled with the first filling structure. The skeletal frame may comprise a plurality of self-expanding struts that are adapted to radially expand outward along with the outer wall of the first filling structure. The skeletal frame may comprise a wire-like helically shaped filament made from a material such as nitinol.

The sealing feature may also comprise an upper and a lower tubular shaped cuff that is coupled with the first filling structure. At least one of the upper or lower cuffs may comprise a reinforced region. The reinforced region may comprise a wire-like frame and sometimes the upper and lower reinforced cuffs may be coupled together with a plurality of struts.

In still other embodiments, the sealing feature may comprise a pair of fillable legs that are coupled with the first filling structure. The sealing feature may comprise a first region of the first filling structure having a first compliance and a second region of the first filling structure having a second compliance different than the first compliance. One of these regions may be embossed and another region may remain unembossed.

The system may further comprise a delivery catheter that has an expandable tubular support such as a balloon, which can be positioned within the tubular lumen to carry the double-walled filling structure. The system may also comprise a scaffold that is radially expandable from a collapsed configuration to an expanded configuration. A filling port that is fluidly coupled with the filling structure may also be included in the system. The filling port may be an elastomeric plug, and may be adapted to receive the hardenable filling medium and also provides a seal to prevent leakage thereof. The filling port may be substantially contained within the inner lumen of the filling structure when the filling structure is filled with the hardenable filling medium.

In another embodiment of the invention, a system for treating an aneurysm comprises at least a first double-walled filling structure having an outer wall and an inner wall. The filling structure is adapted to be filled with a hardenable fluid filling medium so that the outer wall conforms to the inside surface of the aneurysm and the inner surface forms a generally tubular lumen to provide blood flow. The system also includes a filling port that is substantially contained within the generally tubular lumen of the filling structure when the filling structure is filled with the hardenable fluid filling medium. A first end of the generally tubular lumen may comprise an invaginated tapered portion that flares radially outward. A second end of the tubular lumen may comprise an invaginated tapered portion that flares radially outward. The second end may be opposite of the first end. The first filling structure may comprise a sealing feature that forms a fluid seal between the filling structure and the aneurysm or an adjacent endograft when the filling structure is filled with the hardenable fluid filling medium. This reduces or prevents blood flow downstream of the seal. The sealing feature may comprise a tapered shoulder region on at least one end of the filling structure. The outer wall of the filling structure may be invaginated into the filling structure thereby forming a convex exterior surface on one end of the filling structure when the filling structure is filled with the hardenable fluid filling medium. A convex exterior surface may also be similarly formed on a second end of the filling structure opposite the first end. Either convex exterior surface may taper radially inwardly to merge with the tubular lumen.

These and other embodiments are described in further detail in the following description related to the appended drawing figures.

BRIEF DESCRIPTION OF THE DRAWINGS

FIGS. 4H-1 and 4H-2 are cross-sectional views taken along line 4H1-4H1 or 4H2-4H2 in FIG. 4H.

FIGS. 5A-5B illustrate one embodiment of a double-walled filling structure.

FIGS. 5C-5E illustrate an exemplary method of fabricating the filling structure in FIGS. 5A-5B.

FIG. 5F illustrates a filling port.

FIGS. 6A-18 illustrate alternative embodiments of a double-walled filling structure.

FIGS. 33A-33B illustrate another embodiment of a filling structure.

FIGS. 34A-34D illustrate the use of multiple filling structures stacked together.

DETAILED DESCRIPTION OF THE INVENTION

Figure 1:
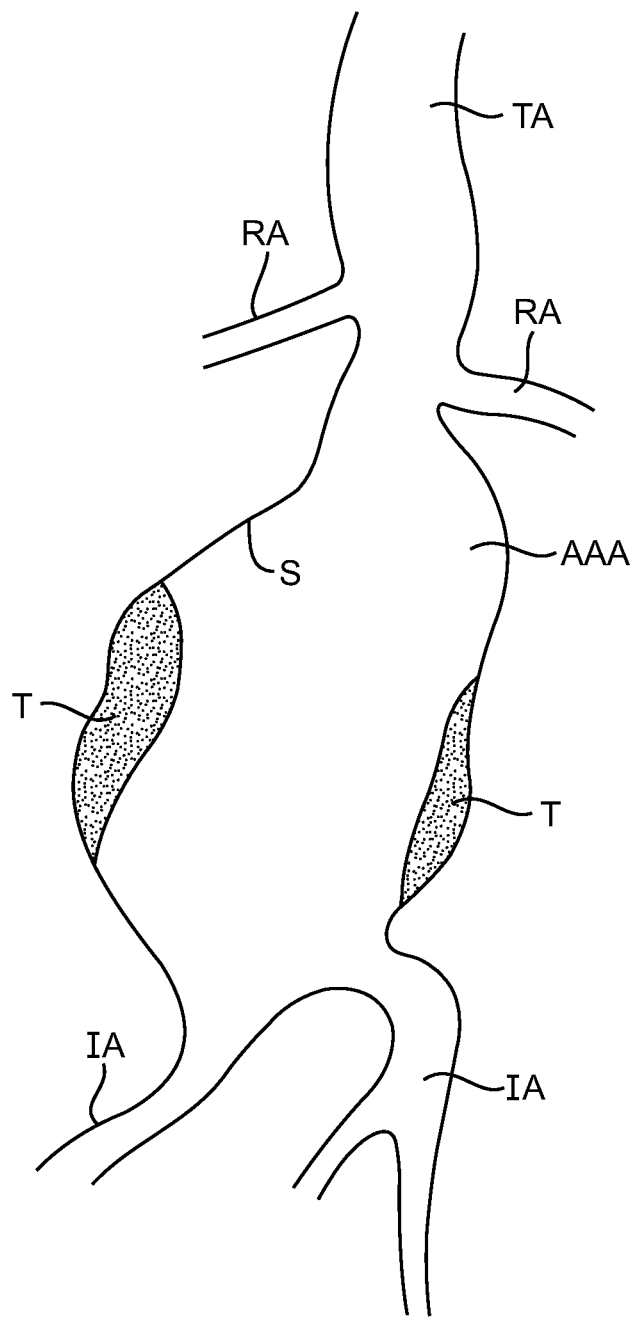
FIG. 1 illustrates the anatomy of an infrarenal abdominal aortic aneurysm.

Referring now to FIG. 1, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 2:
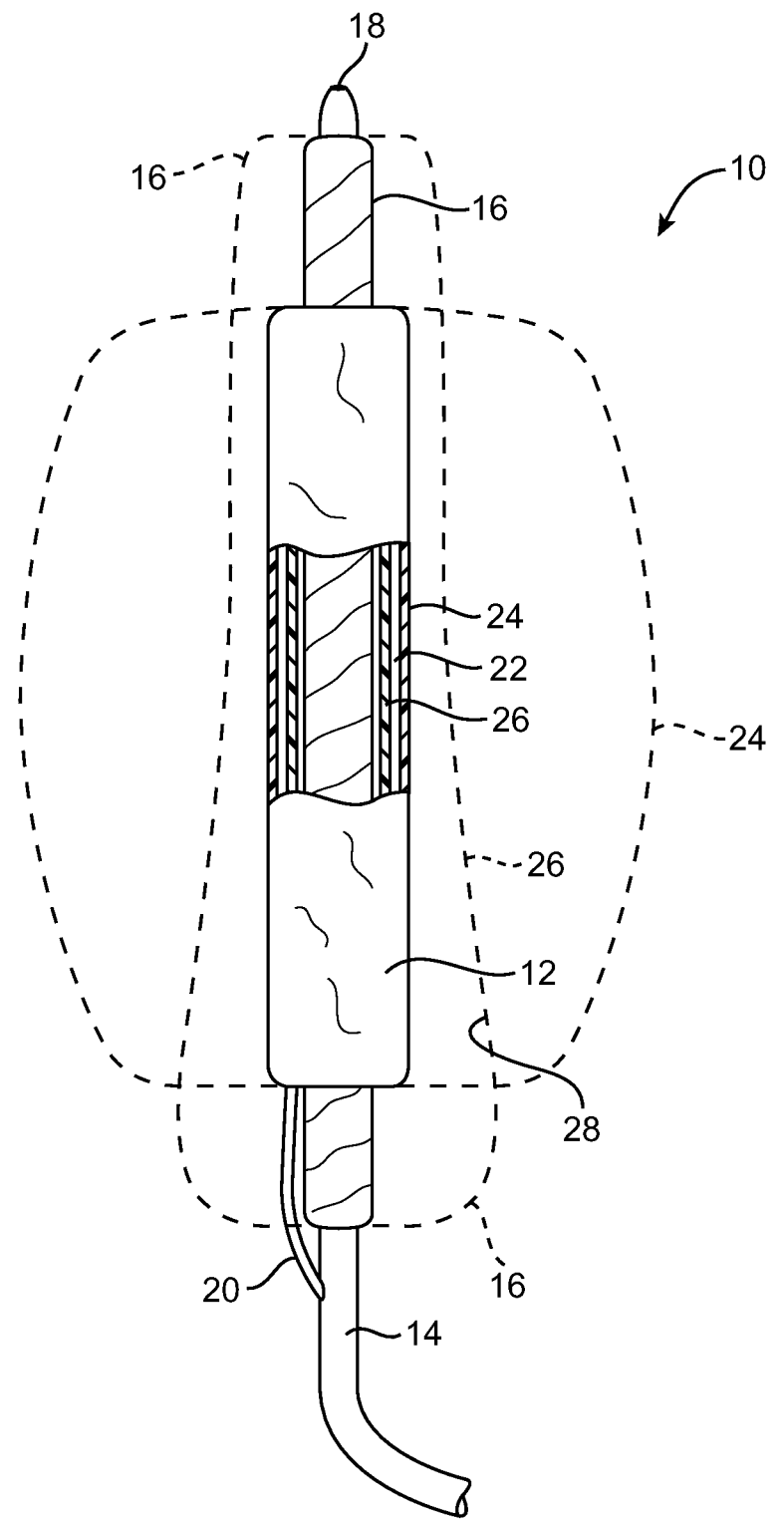
FIG. 2 illustrates a single prosthesis system comprising a filling structure mounted over a delivery catheter.

FIG. 2 illustrates a single endograft system comprising a filling structure mounted over a delivery catheter. A system 10 constructed in accordance with the principles of the present invention for delivering a double-walled filling structure 12 to an aneurysm includes the filling structure and a delivery catheter 14 having an expandable element 16, typically an inflatable balloon, at its distal end. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall will expand radially outwardly, as shown in broken line, as will the inner wall 26, also shown in broken line. Expansion of the inner wall 26 defines an internal lumen 28. The expandable balloon or other structure 16 will be expandable to support an inner surface of the lumen 28, as also in broken line in FIG. 1. A single endograft system such as that seen in FIG. 1 may be used to treat an aneurysm as disclosed in U.S. patent application Ser. No. 11/413,460, the entire contents of which are incorporate herein by reference.

Figure 3:
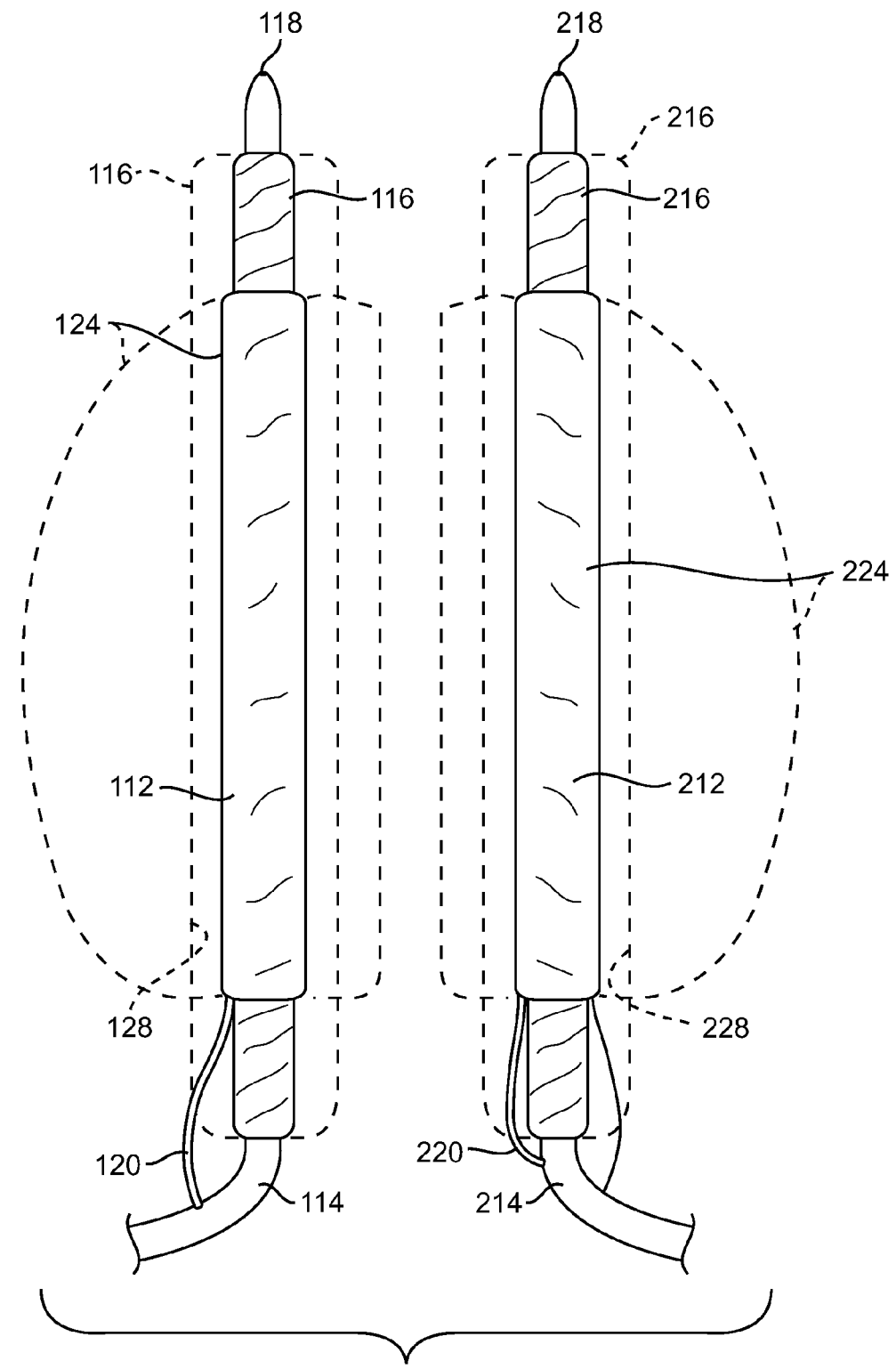
FIG. 3 illustrates a pair of prostheses for delivery to an aneurysm, where each prosthesis comprises a filling structure mounted on a delivery catheter.

In preferred embodiments, a system comprising two endografts may be used to treat an aneurysm, such as the system seen in FIG. 3. A system comprising such a pair of filling structures includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 2. Corresponding parts of each of the fillings systems 112 and 212 will be given identical numbers with either the 100 base number or 200 base number. A principal difference between the filling structures 112 and 212, on the one hand, and the filling structure 12 of FIG. 2 is that the pair of filling structures will generally have asymmetric configurations which are meant to be positioned adjacent to each other within the aneurismal space and to jointly fill that space, as will be described in greater detail below.

Figure 4A:
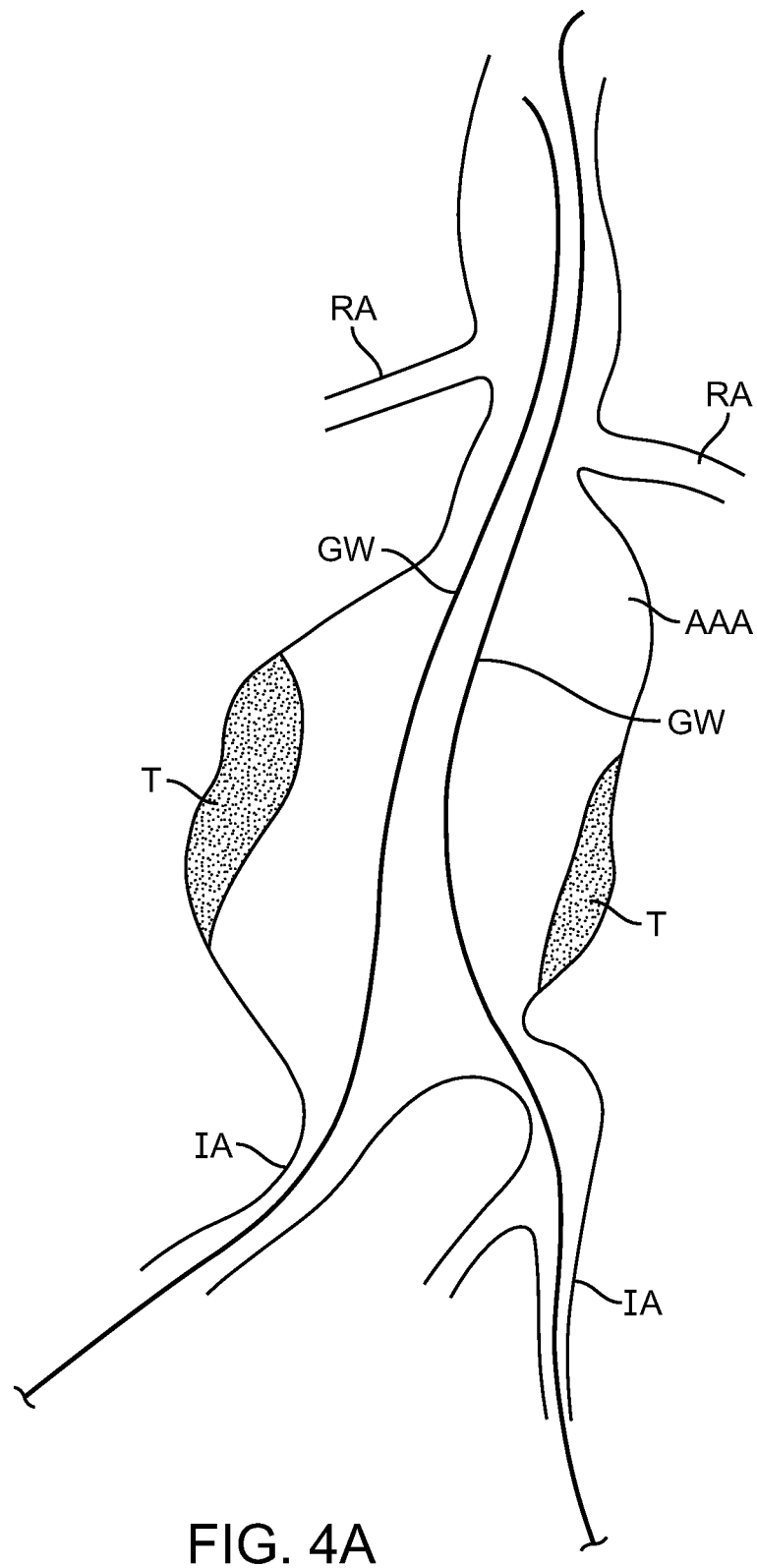
FIGS. 4A-4F illustrate use of the filling structures of the prosthesis system in FIG. 3 for treating an aortic aneurysm.
Figure 4B:
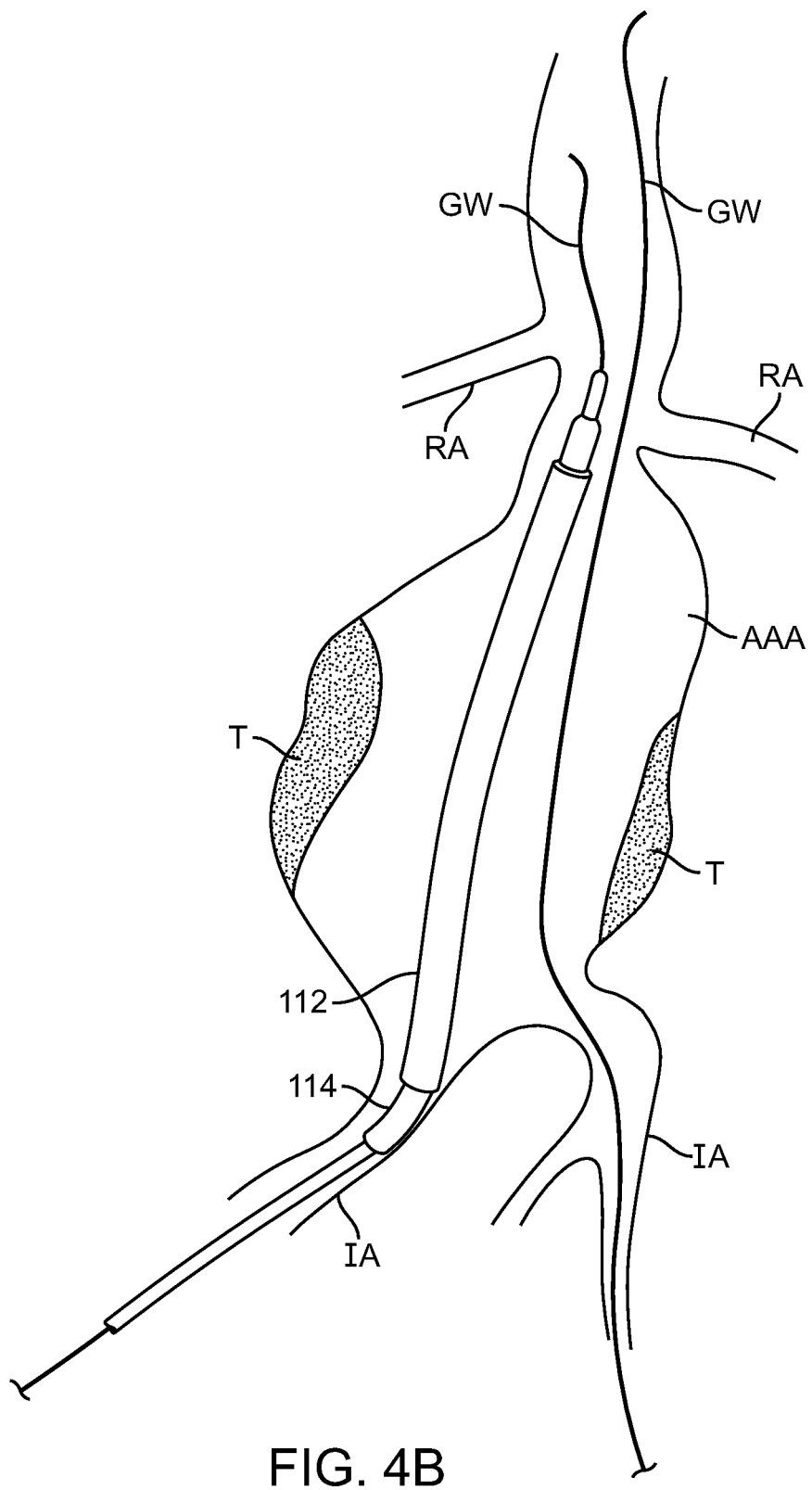
Figure 4C:
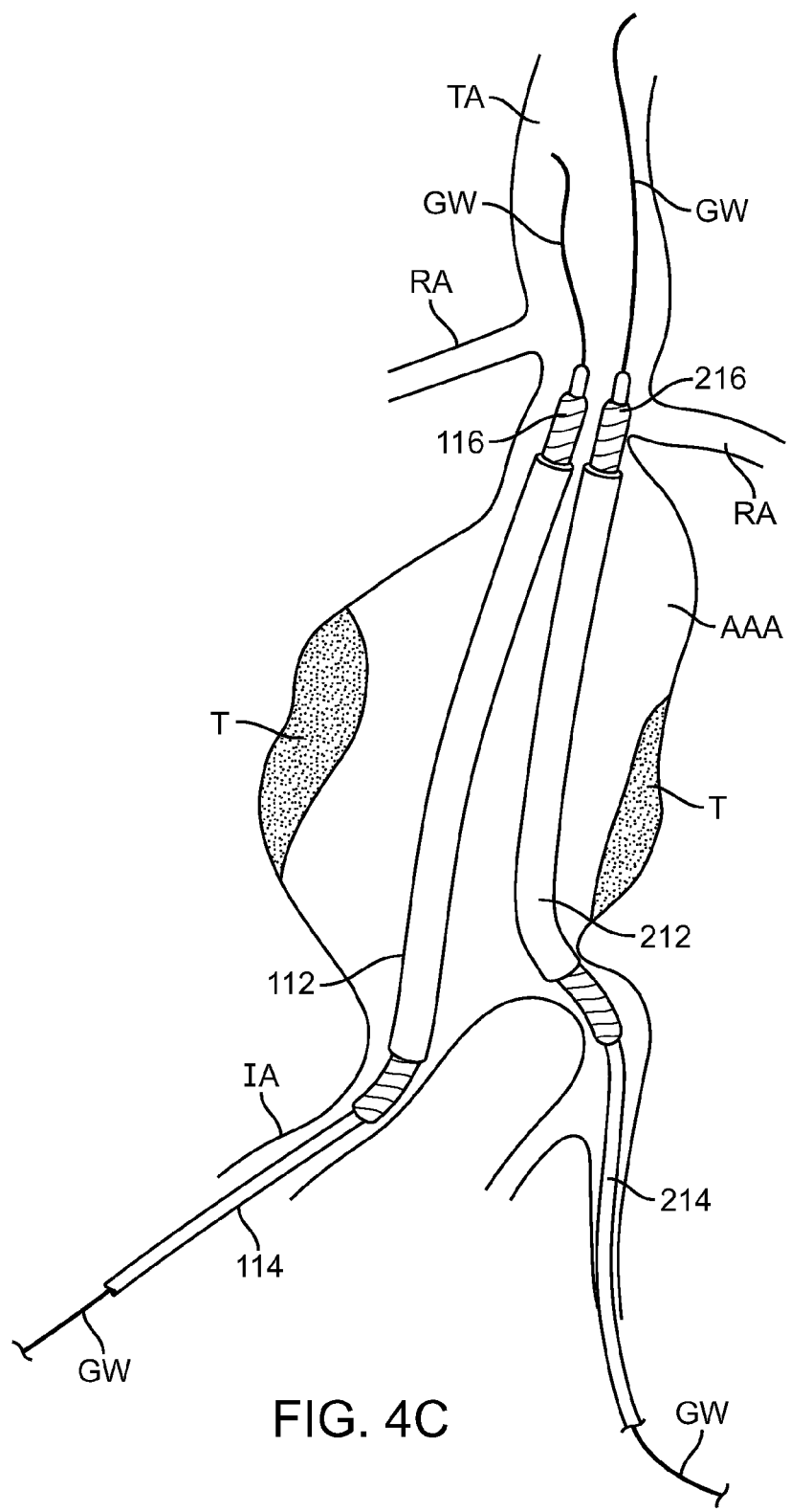
Figure 4D:
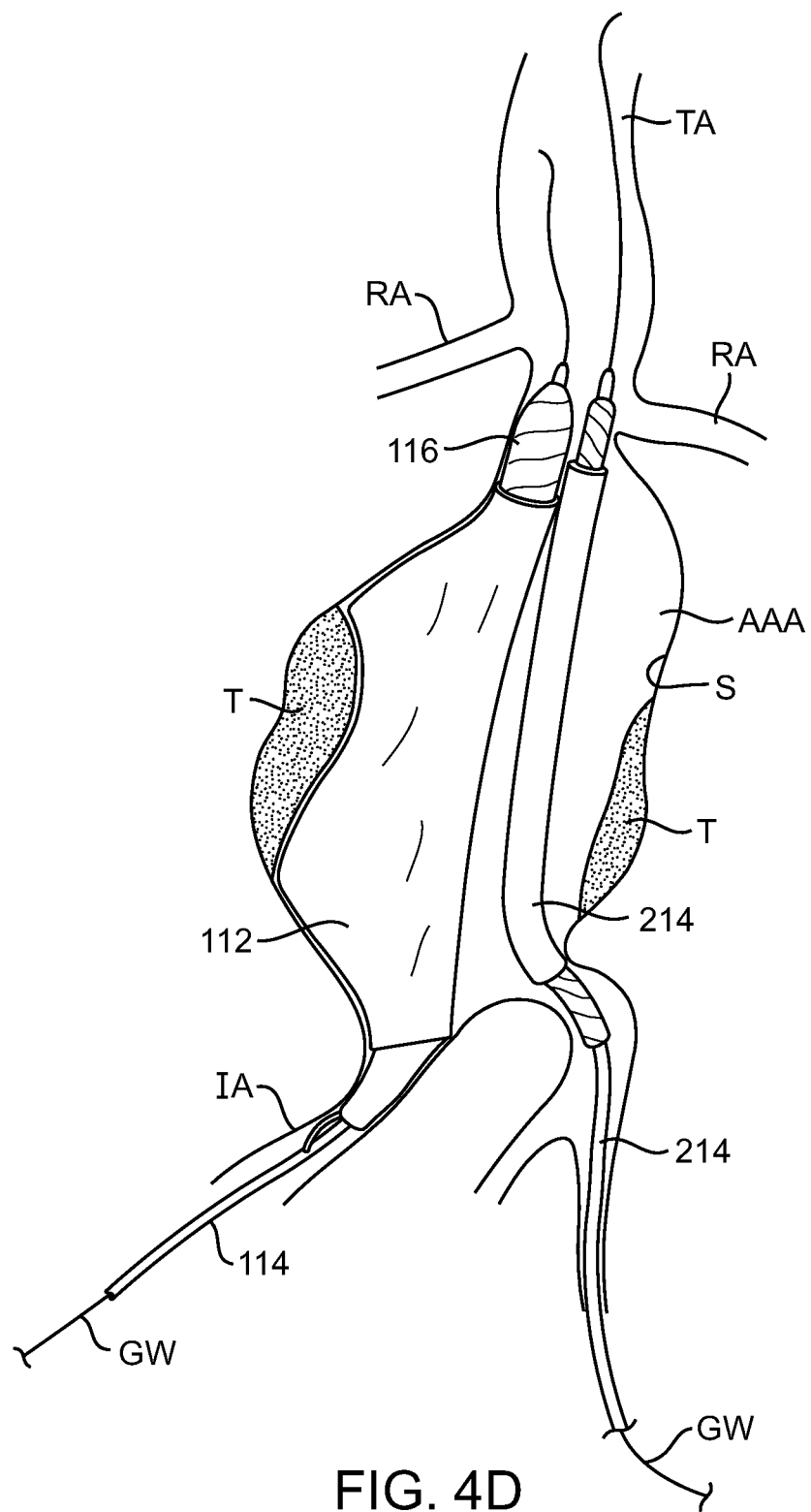
Figure 4E:
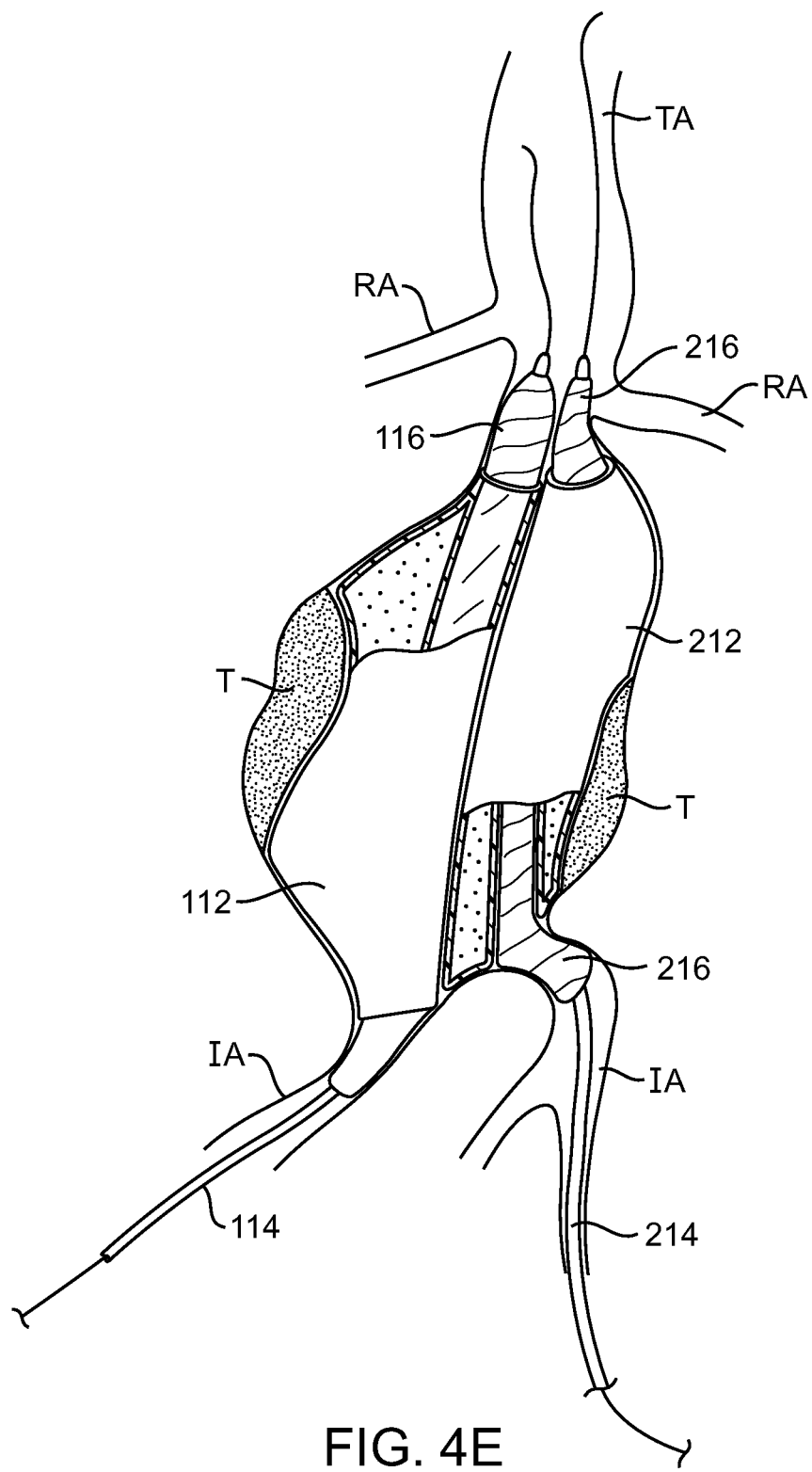

In treating an infrarenal abdominal aortic aneurysm using the pair of filling structures 112 and 212 illustrated in FIG. 3, a pair of guidewires (GW) will first be introduced, one from each of the iliac arteries (IA), as seen in FIG. 4A. The first delivery catheter 114 will then be positioned over one of the guidewires to position the double-walled filling structure 112 across the aortic aneurysm (AAA), as illustrated in FIG. 4B. The second delivery catheter 214 is then delivered over the other guidewire (GW) to position the second filling structure 212 adjacent to the first structure 112 within the aneurysm (AAA), as illustrated in FIG. 4C. Typically, one of the filling structures and associated balloons will be expanded first, followed by the other of the filling structures and balloon, as illustrated in FIG. 4D where the filling structure 112 and balloon 116 are inflated to fill generally half of the aneurismal volume, as illustrated in FIG. 4D. Filling can generally be carried out as described for one filling structure in U.S. patent application Ser. No. 11/413,460 which has been previously incorporated herein by reference, except of course that the filling structure 112 will be expanded to occupy only about one-half of the aneurismal volume. After the first filling structure 112 has been filled, the second filling structure 212 may be filled, as illustrated in FIG. 4E. In other protocols the two filling structures may be filled simultaneously. The upper ends of the balloons 116 and 216 will conform the tubular lumens of the filling structures against the walls of the aorta as well as against each other, while the lower ends of the balloons 116 and 216 will conform the tubular lumens into the respective iliac (IA).

Figure 4F:
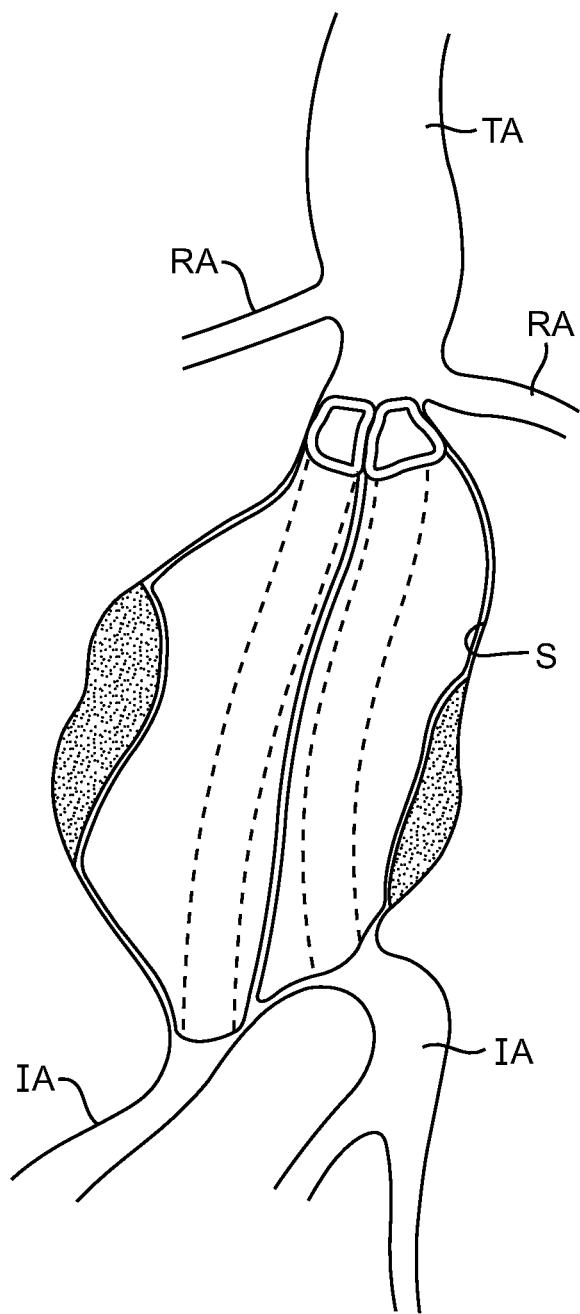

After filling the filling structures 112 and 212 as illustrated in FIG. 4E, the filling materials or medium will be cured or otherwise hardened, and the delivery catheters 114 and 214 removed, respectively. The hardened filling structures will then provide a pair of tubular lumens opening from the aorta beneath the renal arteries to the right and left iliac arteries, as shown in broken line in FIG. 4F. The ability of the filling structures 112 and 212 to conform to the inner surface (S) of the aneurysm, as shown in FIG. 4F, helps the structures to remain immobilized within the aneurysm with little or no migration. Immobilization of the filling structures 112 and 114 may be further enhanced by providing any of the surface features described in U.S. patent application Ser. No. 11/413,460, previously incorporated herein by reference.

As with the single filling structure embodiments, the double filling structure embodiments will include at least one separate scaffold deployed within each of the tubular blood flow lumens. The scaffolds will generally be stent-like or graft-like vascular structures and will be deployed within the tubular lumens using balloon or other expansion catheters (in the case of malleable or balloon-expandable scaffolds) or using constraining sheaths (in the case of self-expanding scaffolds).

Figure 4G:
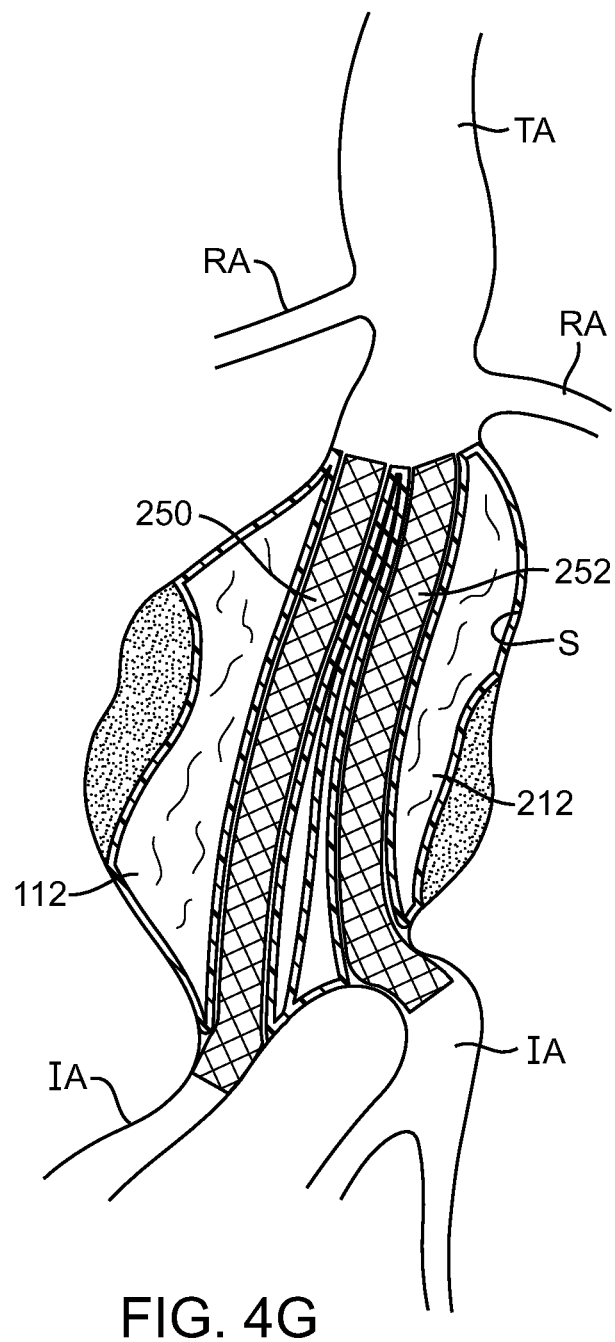
FIGS. 4G-4H illustrate the placement of scaffolds into the adjacent tubular lumens of the two filling structures of the prostheses of FIGS. 4A-4F.

Referring in particular to FIG. 4G, the first scaffold 250 may be placed in the tubular lumen of the first filling structure 112 while a second scaffold 252 may be placed in the tubular lumen of the second filling structure 212. As illustrated, the scaffolds are stent-like structures which extend into the iliac arteries IA at the lower end of the filling structures. The scaffolds 250, 252 may also be deployed simultaneously with the filling structures 112, 212.

Figure 4H:
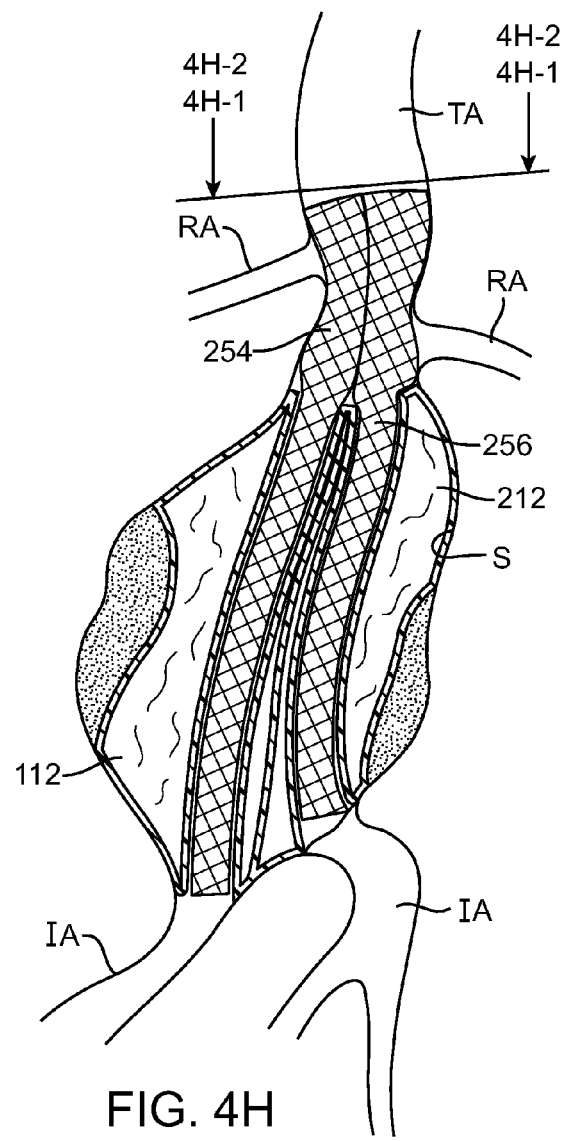
Figures 1, 4H:
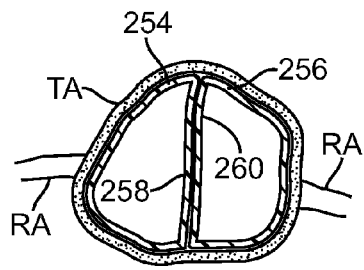
Figures 2, 4H:
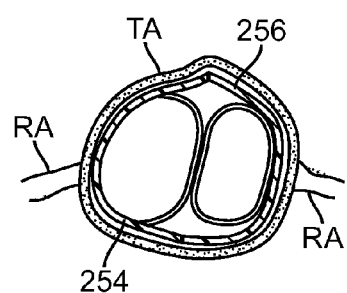

Referring now to FIG. 4H, first and second scaffolds 254 and 256 may extend upwardly on the aortic side of the first and second filling structures 112 and 212. When the separate stent or other scaffold structures extend into the thoracic aorta TA, it will usually be desirable that they be expanded so that they conform to each other along a plane or region of contact. For example, as shown in FIG. 4H-1, the upper ends of the scaffolds 254 and 256 may be formed preferentially to have D-shaped cross-sections when expanded. Thus, flat faces 258 and 260 will engage each other with the remaining portion of the stent conforming to the inner wall of the aorta. In this way, most of the cross-sectional area of the aorta will be covered with the stent, thus enhancing blood flow through the filling structures. Alternatively, as shown in FIG. 4H-2, the upper regions of the scaffolds 254 and 256 may be cut or otherwise modified to form open C-shaped cross-sections. In such cases, the expanded scaffolds can be arranged so that the C-shaped regions engage each other to form a continuous ring structure about the inner wall of the aorta. The open C-shaped regions will transition into a tubular region as the scaffolds enter the tubular lumens of the filling structures 112 and 212. In either of these embodiments, the scaffolds 254 and 256 may be partially or fully covered with a membrane or graft material and such coverings may extend partially or fully over the portion of the scaffold that extends into the adjacent blood vessel.

Various modifications of the protocols described above will be within the scope of the present invention. For example, while the scaffolds have been shown as being delivered after deployment of the filling structure(s), it will also be possible to deliver the scaffolds simultaneously with or prior to deployment of the filling structures. Moreover, the scaffolds could be delivered on the same delivery catheter(s) used to deliver and/or shape the filling structures. The scaffolds could then be expanded at the same time as filling the filling structure or even prior to filling the filling structure. Additional details on these embodiments are disclosed in U.S. patent application Ser. No. 11/413,460, previously incorporated herein by reference.

The filling structure used in FIGS. 4A-4H are more fully described in FIGS. 5A-5E. FIG. 5A illustrates the double-walled filling structure separated from the delivery catheter and scaffold. In FIG. 5A, the outer wall 502 is the portion of the filling structure which expands into engagement with the aneurysm wall when filled with filling material and inner wall forms lumen 504 in which blood traverses the aneurysm. A filling tab FT is coupled with the filling structure and acts as a valve to allow filling of the filling structure. FIG. 5B shows an end view of the filling structure with an oval or elliptical-shaped outer wall 502 and a round inner lumen 504. The walls of the filling structure are preferably made from ePTFE with a polyurethane inner lining which prevents extravasation of the filling material through the pores of the ePTFE. Other polymers or fabrics may also be used such as Dacron polyester. Any of the filling structure embodiments in this disclosure may use these materials.

The filling structure of FIGS. 5A-5B may be fabricated from two sheets of polymer as seen in FIGS. 5C and 5D. In FIG. 5C, an upper sheet is die cut from ePTFE and has an upper flat pan section 508a and a lower handle section 510a. In FIG. 5D, a second sheet is also die cut from ePTFE and also has an upper pan section 508b and a lower handle section 510b. The upper and lower sheets are substantially the same size. The two sheets are then placed on top of one another and the edges are then sealed together around most of the perimeter, as seen by seam 512 in FIG. 5E. The lower handle section is then invaginated and pulled through the flat pan section as indicated by arrow 514. The unsealed portions are then sealed. Sealing may be accomplished using a hot wire, impulse sealing, RF heat sealing or laser welding. This forms the inner lumen of the filling structure, as indicated by dotted lines 504 in FIG. 5A. A filling tube 506 may be used to allow filling of the filling structure as seen in FIG. 5A or a filling port 516 may be used as illustrated in FIG. 5F. The filling port 516 may be an elastomeric plug such as latex or polymer that allows a needle or other tube to penetrate the filling port and that self seals when the needle or tube is withdrawn. This method of fabrication generally applies to any of the embodiments disclosed herein. Other fabrication methods include inverting a tubular extrusion and sealing the ends which is advantageous since it minimizes seams. Also, in some embodiments, the filling structure may be composed of separate components that are joined together. For example, the tubular lumen section may be formed separately and then coupled with the main body of the filling portion.

As previously discussed, these filling structures show promise in the treatment of aneurysms as they help seal the aneurysm and also they help fix an endograft system in place thereby minimizing the possibility of migration. However, the filling structures can still leak. Therefore, other filling structure configurations and features are disclosed herein which may provide better sealing.

Figure 6A:
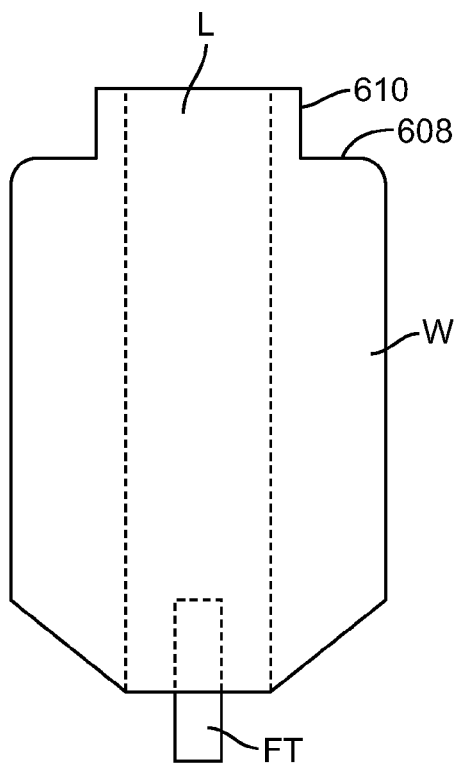
Figure 6B:
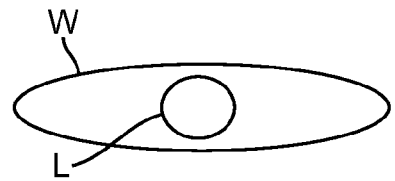
Figure 7A:
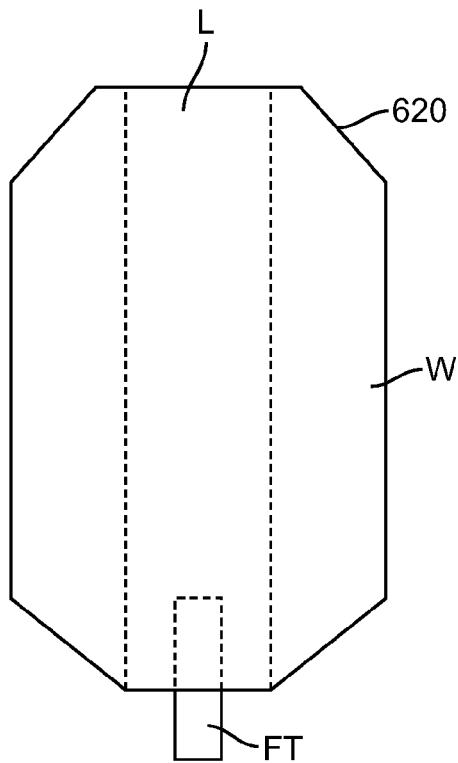
Figure 7B:
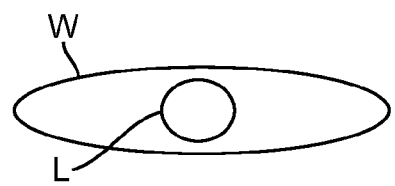

In FIG. 6A, the filling structure has an outer wall W and an inner wall forms the lumen L. This embodiment also includes a flat shoulder 608 and a narrow neck region 610 which may accommodate aneurysm anatomies better and therefore provide better sealing. FIG. 6B shows and end view of the filling structure in FIG. 6A. The neck region may have a width any size, but in preferred embodiments, the width of the neck region 610 is approximately 2% to approximately 20% of the filling structure width measured at it's widest point. FIGS. 7A-7B show another embodiment of a filling structure. In FIG. 7A, a double-walled filling structure includes a tapered upper portion 620 which provides a flat surface against which a seal may be made. FIG. 7B shows an end view of the filling structure seen in FIG. 7A which has a generally oval shape when filled with filling material and the lumen L is generally round.

FIGS. 8A-8B show another embodiment of a filling structure. In FIG. 8A, a first layer of material is welded to a second layer of material that is wider than the first. This results in one side of the filling structure having more material than the opposite side. Therefore, one side of the outer wall W will have a substantially flat section 626 and the opposite side will be arcuate 630 with a straight section 628 joining the two sections together. The end view of the filling structure will be D-shaped as seen in FIG. 8B.

Still another filling structure embodiment is seen in FIGS. 9A-9B. In FIG. 9A the inner wall of the filling structure forms lumen L. Lumen L includes a straight tubular section 642 and a tapered portion 640 near an upper portion of the filling structure. The tapered portion 640 flares radially outward.

FIG. 9B shows an end view of the filling structure seen in FIG. 9A. In FIG. 9B, outer wall W forms a round or oval shape and lumen L is generally round.

FIGS. 10A-10B illustrate the use of additional seals in the filling structure to define additional filling regions. In FIG. 10A, the two layers of material are sealed together along a line 644 forming a pocket 646 which is fillable with the hardenable filling material. In this embodiment, the seal 644 is seen running across both the left and right halves of the filling structure and in a direction generally transverse to the longitudinal axis of the filling structure. The length of the seal, number of seals and angle of the seal relative to the filling structure longitudinal axis may be varied. Also, in this embodiment, the pocket 646 is still in fluid communication with the main fillable region of the filling structure. FIG. 10B illustrates an end view of the filling structure seen in FIG. 10A.

In FIG. 11, two filling structures are used to complement one another and help for a seal. In FIG. 11, a first filling structure has an outer wall with a taper 652 and a generally tubular lumen L. A second filling structure has an outer wall W with a taper 654 that is complementary to the first taper 652, therefore the two filling structures will engage one another where the two tapers meet. Because the two tapers are complementary with one another, they will be flush against one another. The use of two filling structures may be used when two endograft systems are deployed in an aneurysm, such as in FIGS. 4A-4G above.

FIG. 12 shows a foam filled region 660 near an upper portion of the filling structure. The foam filled region 660 is separated from the remainder of the fillable space by a seal 662 which may be made by heat sealing, bonding or other attachment methods known in the art. The foam filled region provides a compliant end that allows the filling structure to conform to the aneurysm anatomy thereby helping create a seal.

FIG. 13 shows an alternative embodiment of a filling structure having a flexible arm 666 coupled with the filling structure. A slot 668 separates the arm 666 from the main body of the filling structure, although a channel 670 fluidly couples the arm 666 with the main body of the filling structure. Therefore, as the filling structure is filled with hardenable medium, the arm 666 will also fill up. The arm is flexible and therefore will flex and fit into various aneurysms spaces thereby creating the seal.

FIG. 14 illustrates an angled filling structure. In FIG. 14, a bottom edge 680 of the filling structure is angled relative to the top edge 682. In this embodiment, the bottom edge 680 forms an acute angle relative to the top edge 682 although the angle may be adjusted to accommodate different aneurysm anatomies.

FIG. 15 illustrates the use of two filling regions in the filling structure. In FIG. 15, the filling structure has a main filling region 688 and a separate, discrete filling region near a top of the filling structure. A filling tab FT is fluidly coupled with both fillable regions 686, 688, thus a filling tube may be slidably received by the upper filling region 686. After this region is filled, the filling tube is retracted out of the upper filling tab and into the lower filling tab so that the main filling region can then be filled. The upper filling region may be created by sealing a region off from the main body of the filling structure. This two stage filling process may allow the filling structure to create a better seal with the aneurysm.

Figure 16:
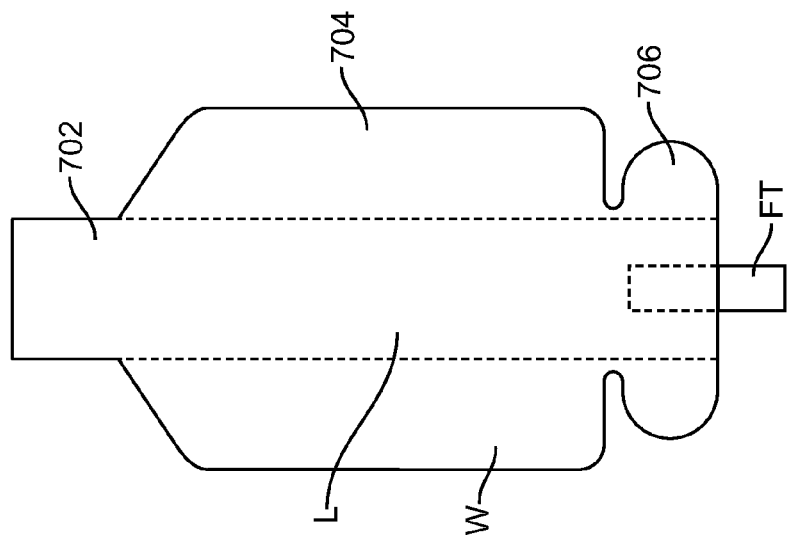

FIG. 16 illustrates still another embodiment of a double-walled filling structure. In FIG. 16, the filling structure comprises a wide main body section 704 and a narrow neck region 702 on an upper end of the filling structure. A lower end of the filling structure has an annular flange 706 that has a width less than the main body section 704. This helps prevent or minimize pinching in the lower end of the filling structure and may help the filling structure accommodate various aneurysm anatomies.

Figure 17:
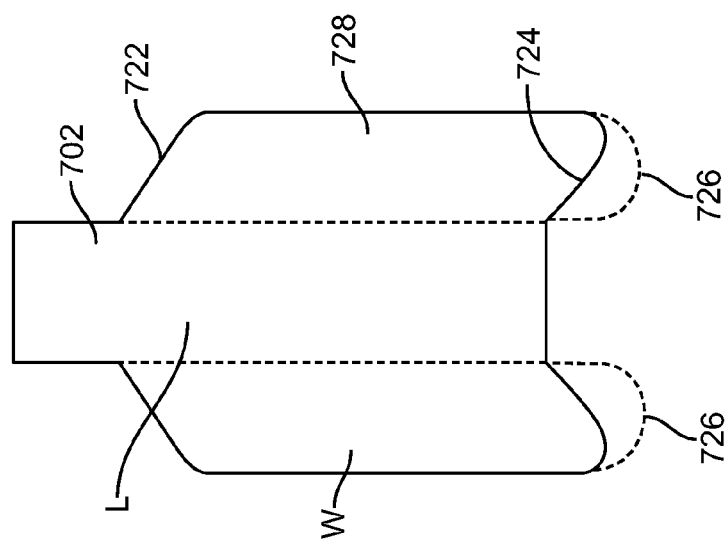

FIG. 17 illustrates another embodiment of a double-walled filling structure. In FIG. 17, the filling structure has a wide main body section 728, a shoulder region 722 and a narrow neck region 720. Additionally, a concave bottom region 724 of the filling structure may expand outward when filled as indicated by dotted line 726.

Figure 18:
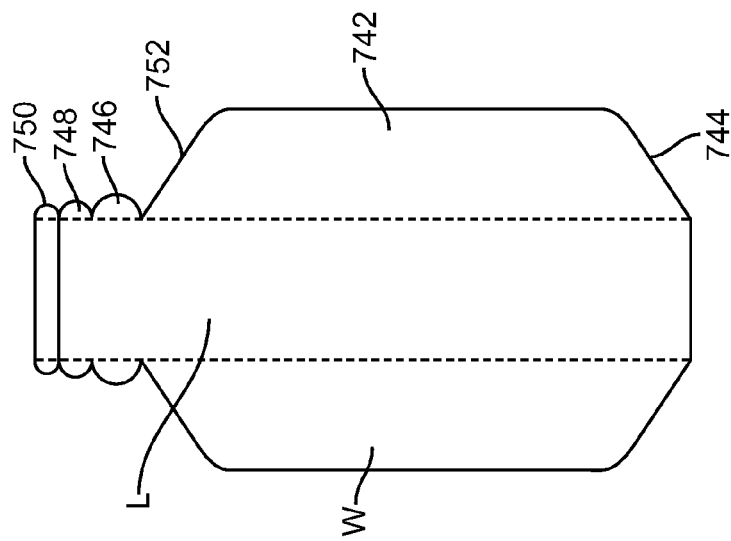

FIG. 18 shows another filling structure embodiment having multiple annular flanges. In FIG. 18, the filling structure comprises a wide main body section 742 and a tapered lower region 744. The main body section has a tapered shoulder region 752 which transitions into a region of multiple annular flanges. A first annular flange 746 is followed by two additional annular flanges 748, 750. The width and thickness of each flange progressively decreases such that flange 746 is the widest and thickest while flange 750 is the thinnest. The multiple flanges help create a seal at one end of the filling structure by minimizing pinch points.

Figure 19A:
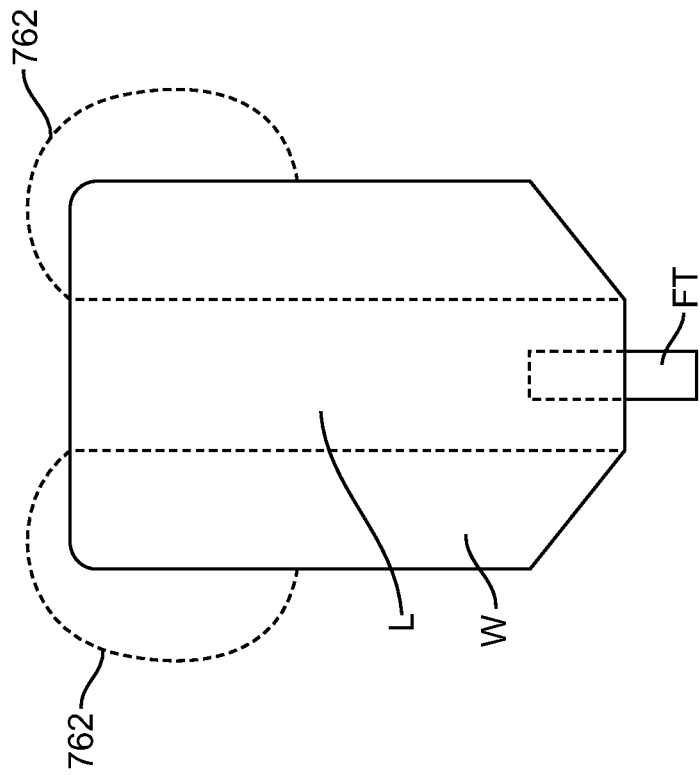
FIGS. 19A-20 illustrate filling structures with regions of different compliance.
Figure 19B:
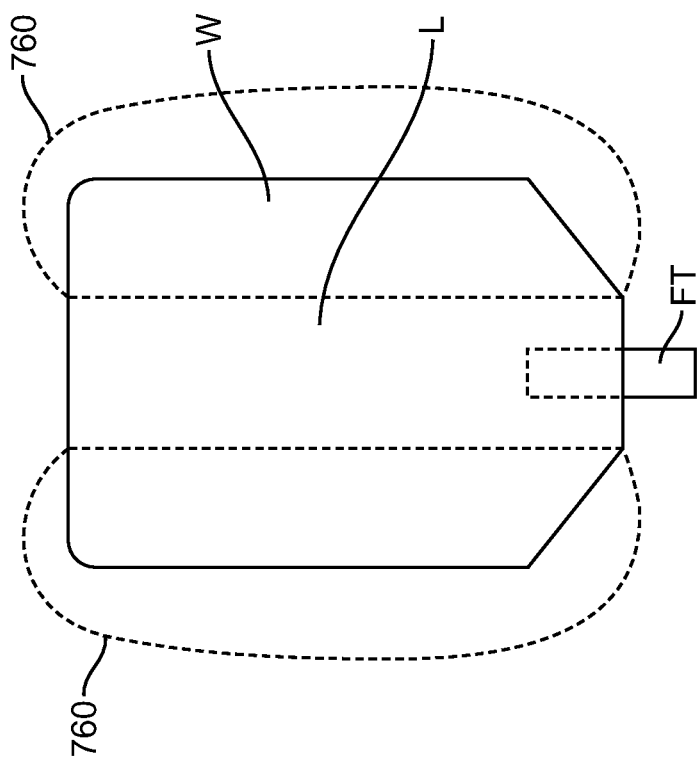
Figure 20:
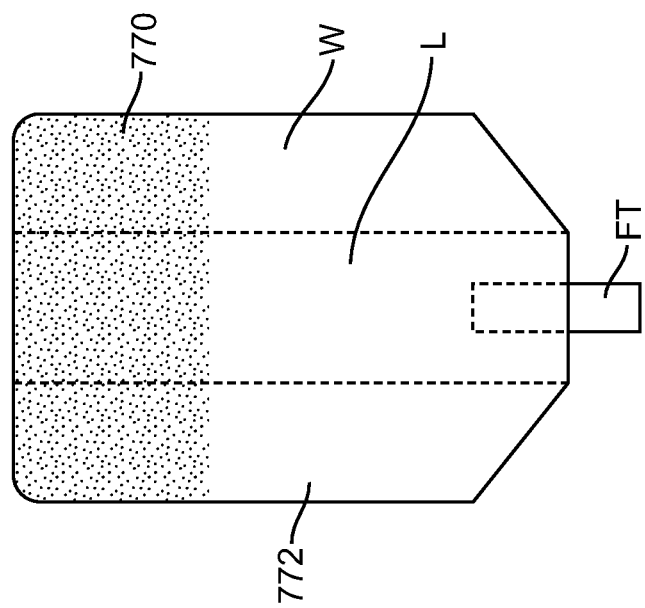

FIGS. 19A-19B illustrate how the compliance of the filling structure may be modified to affect how it expands. In FIG. 19A, the wall forming the inner lumen L may be made from a material having one compliance and the wall forming the outer wall W may be made from a material having greater compliance. Thus, when the filling structure is filled with the hardenable filling material, the outer wall will preferentially radially expand outward before the inner lumen wall. Thus, the lumen will remain relatively unchanged during filling and the outer wall will conform to the aneurysm. In FIG. 19B, the upper half of the outer wall of the filling structure is fabricated from a material more compliant relative to the lower half of the filling structure. Thus, the upper outer half 762 will radially expand more than the lower half during filling. One will appreciate that compliance of the filling structure walls may be varied to obtain desired expansion characteristics. Instead of using different materials to control filling structure compliance, surface modification may be used to alter a material's compliance. For example, in FIG. 20, an upper portion 770 of a filling structure has been embossed while a lower portion 772 remains unembossed. Embossing the material alters material characteristics such as compliance. In the case of expanded polytetrafluorinated ethylene (ePTFE), embossing increases material compliance so region 770 will have a greater compliance and expand more than the unembossed region 772.

Figure 21:
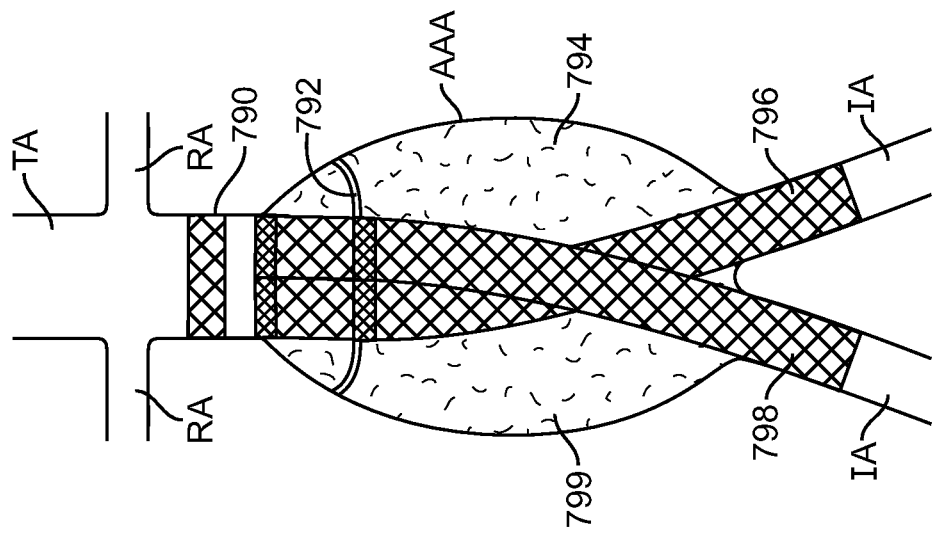
FIG. 21 illustrates a system for treating an aneurysm having three endografts.

While most of the filling structure embodiments disclosed above are described as being used when two endograft systems are deployed (e.g. FIG. 3) to treat an aneurysm, the embodiments described above may also be used in other endograft systems as well. For example, in some cases, it may be desirable to use a three piece endograft system to treat an aneurysm, such as in FIG. 21. In FIG. 21, a first docking scaffold 790 is deployed in the neck of the aneurysm AAA and an optional filling structure 792 may be used to seal the neck region off from blood flow. Two leg extension scaffolds 796 and 798 are then advanced an expanded at least partially within the docking scaffold 790. The leg scaffolds 796 and 798 may also have optional filling structures 794, 799 which may be expanded with hardenable filling material to fill the aneurismal space. Additional details on the three piece endograft system is disclosed in U.S. Provisional Patent Application No. 61/052,059, the entire contents of which are incorporated herein by reference. The filling structures previously described may therefore be used in conjunction with the docking scaffold or either leg extension scaffold. Additional filling structure embodiments which may be used in the three piece docking system or the two piece system previously described are discussed in greater detail below.

Figure 22:
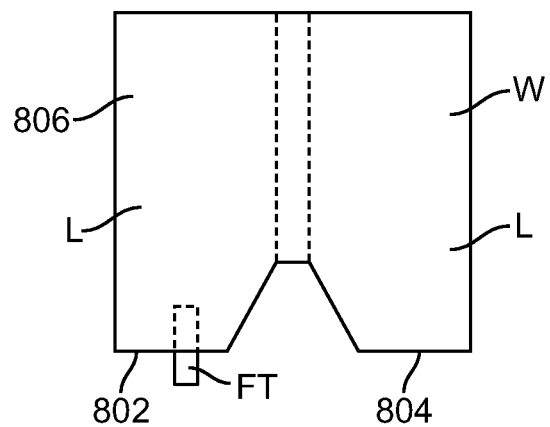
FIGS. 22-26B illustrate various embodiments of filling structures that may be used in the endograft system of FIG. 21.
Figure 23:
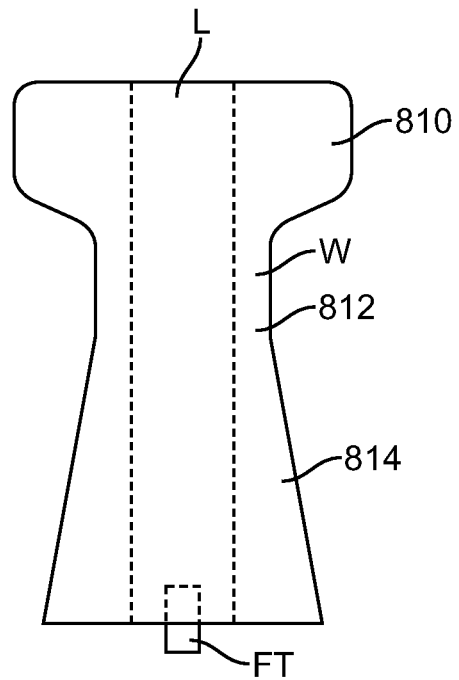
Figure 24A:
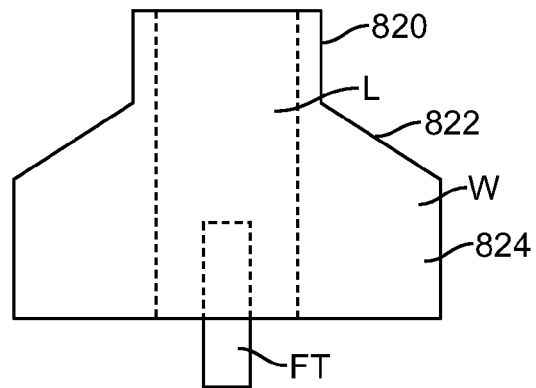
Figure 24B:
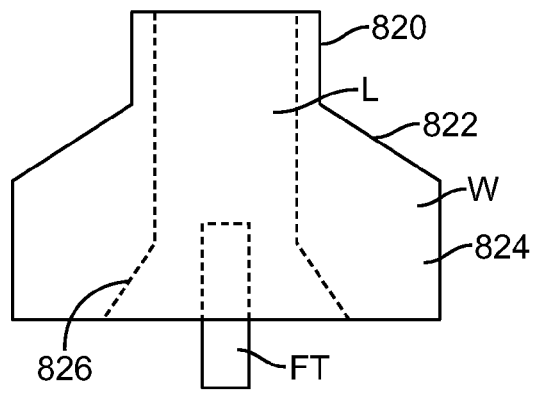
Figure 24C:
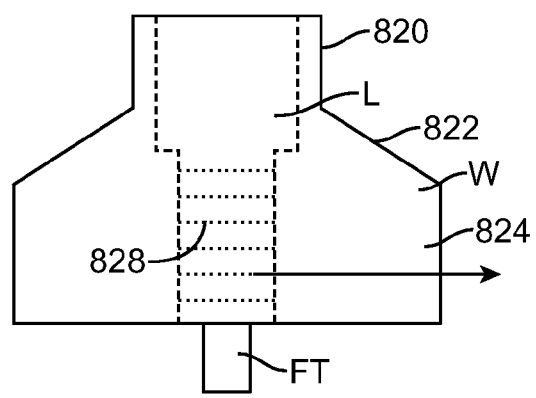

FIG. 22 shows an embodiment of a filling structure having two legs 802, 804. In FIG. 22, the main body 806 of the filling structure may be coupled with the docking scaffold to help seal at the neck of the aneurysm. Two leg regions 802, 804 help to seal around the leg extension scaffolds that are received by the docking scaffold. FIG. 23 shows another embodiment of a filling structure which may be used in conjunction with a docking scaffold. In FIG. 23, the filling structure has a main body region 812 with an enlarged head region 810 and a tapered lower region 814. The enlarged head region 810 and the tapered lower region 814 help seal the docking scaffold around the neck of the aneurysm. FIGS. 24A-24C illustrate other embodiments which may be used with the docking scaffold. For example, in FIG. 24A a filling structure has a main body portion 824 with a tapered shoulder 822 and a narrow neck region 820. The inner lumen L in the embodiment of FIG. 24A is substantially tubular and has a constant diameter. In FIG. 24B, the filling structure has generally the same shape as in FIG. 24A except in this embodiment, the lumen L is tapered outwardly 826 near a lower end of the filling structure. The embodiment of FIG. 24C is also similar to that of FIG. 24A but also has a modified lumen L. In FIG. 24C, the filling structure lumen L has a lower portion that is constrained 828 in order to limit its expansion. The constraint 828 may be a band or corset coupled with the inner wall, or a low compliance material may be used in that region to limit expansion of the lumen L.

Figure 25A:
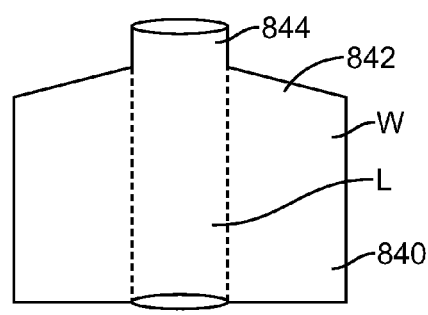
Figure 25B:
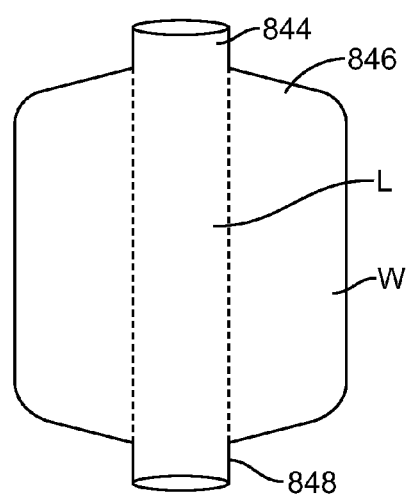
Figure 25C:
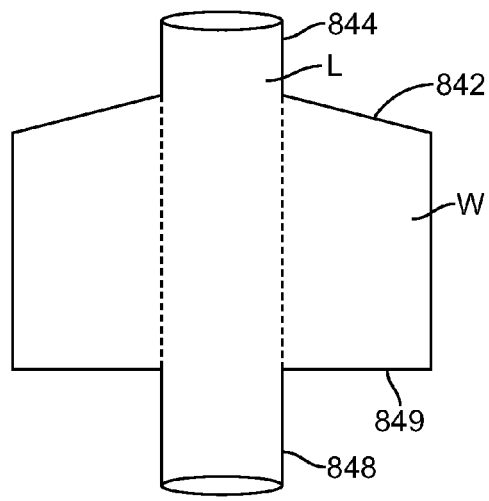

FIGS. 25A-25C illustrate still other embodiments of filling structures which may be used with the docking scaffold. In FIG. 25A, the filling structure comprises a main body section 840 with a tapered shoulder 842 that transitions to a narrow neck region 844. FIG. 25B is similar to the embodiment of FIG. 25A except that both ends of the filling structure have a narrow neck region 844, 848 coupled with the main body of the filling structure. A flat or tapered shoulder region 846 may couple the narrow neck region 844, 848 with the main body of the filling structure. FIG. 25C shows another variation of the embodiment in FIG. 25A. In FIG. 25C, the filling structure has narrow neck regions 844, 848 coupled to the main body of the filling structure. A tapered shoulder region 842 couples the upper narrow neck region 844 with the filling structure main body and a flat lower shoulder 849 couples the lower narrow neck region 848 with the main body of the filling structure.

Figure 26A:
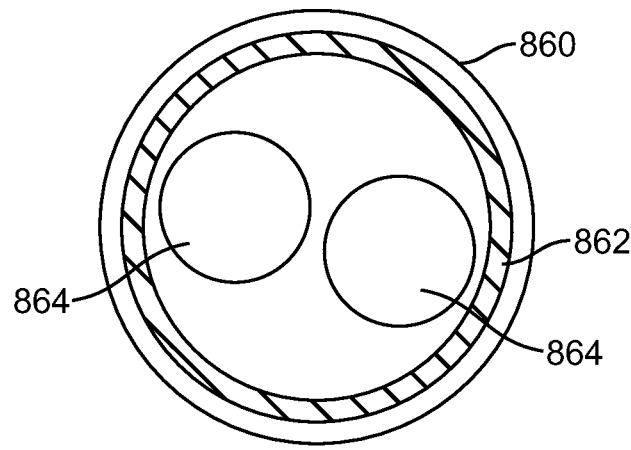
Figure 26B:
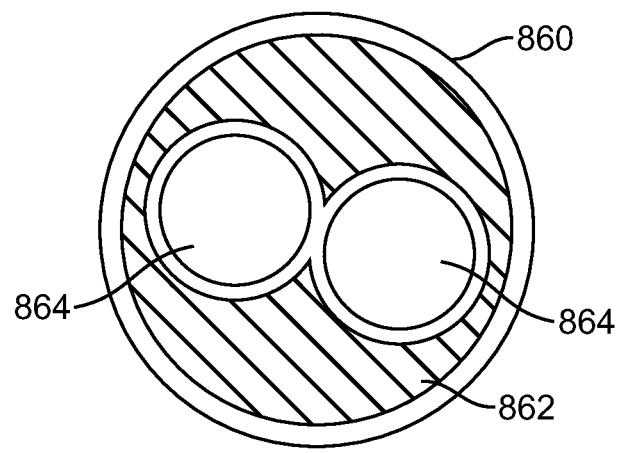

The previous embodiments generally are disposed over a scaffold structure and radially expand outward to seal against the aneurysm wall. In FIGS. 26A-26B, a filling structure is used to fill the internal space of the docking scaffold. FIG. 26A illustrates a top view of a docking scaffold. In FIG. 26A, a double-walled filling structure 862 is coupled to the internal surface of the docking scaffold 860. Two leg extension scaffolds 864 are slidably received by the docking scaffold 860. In FIG. 26B, the filling structure 862 is filled with a hardenable filling medium. The external wall of the filling structure 862 radially expands outward to engage and seal against the inner surface of the docking scaffold 860. The inner wall of the filling structure 862 radially expands inward to seal around the leg extension scaffolds 864.

Figure 28:
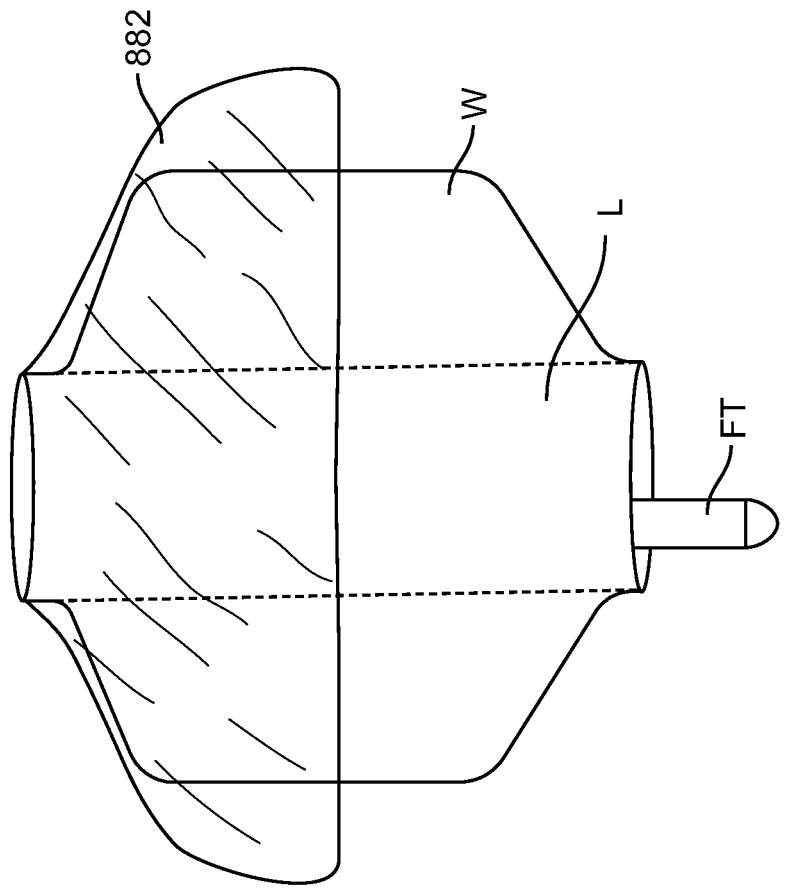
FIGS. 27-29 illustrate various thrombogenic features used to help create a seal.
Figure 27:
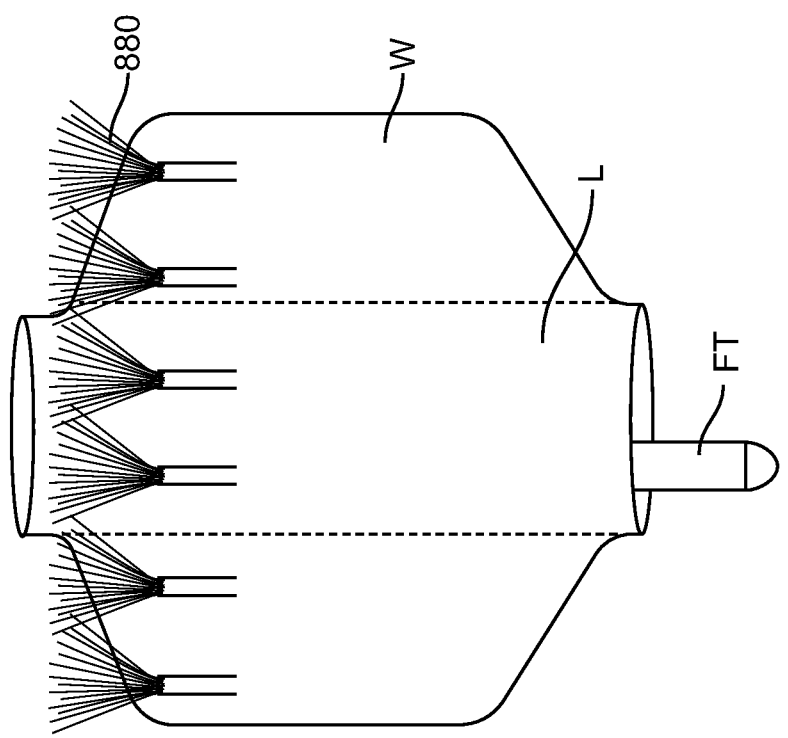
Figure 29:
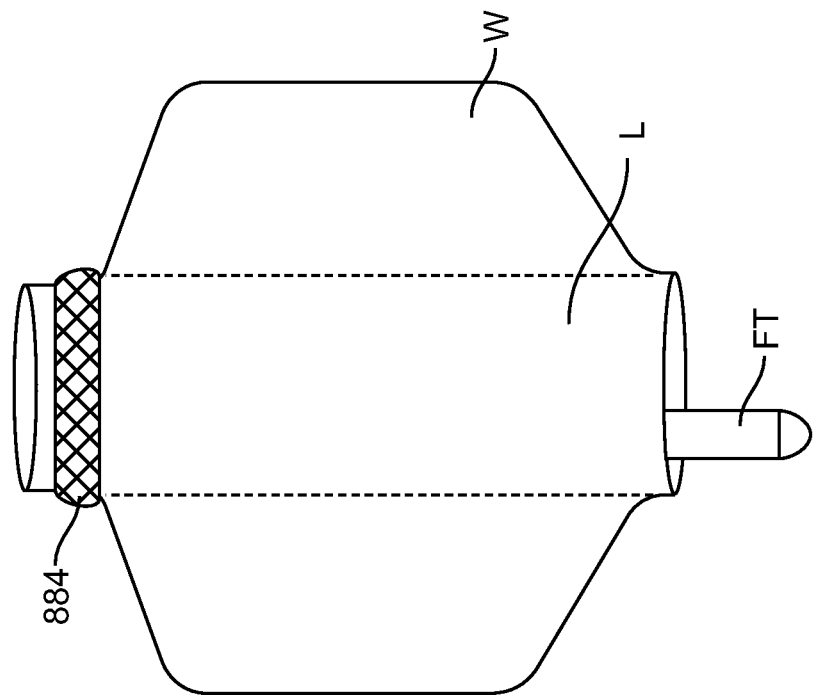

The embodiments described above generally rely on radial expansion of a filling structure to form a seal. The use of thrombogenic materials in combination with a filling structure enhances the resulting seal. In FIG. 27, the filling structure has a plurality of filament-like hairs 880 coupled to an upper portion of the filling structure. These hairs 880 may be made of any thrombogenic material such as those disclosed herein or other materials known in the art. Additionally, the hairs 880 may be coupled with a thrombogenic agent to further cause clotting. The hairs 880 cause blood to clot thereby further sealing the aneurysm. The hairs 880 may be glued, bonded, welded, heat sealed, sintered, sutured, electrospun, sprayed, vapor deposited, drape coated, press fit or otherwise attached to the filling structure. Exemplary materials for hairs 880 include but are not limited to polyurethanes, polycarbonates, polyesters such as Dacron, ePTFE, polyolefins, parylenes, gelatins, silicones, etc. The hair-like structures 880 may be formed into sutures, felts, velours, weaves, knits, hyodrogels, foams, embolization coils or sheets that are attached to the filling structure. FIG. 28 shows an alternative embodiment of a filling structure having a thrombogenic material attached thereto. In FIG. 28, a cape 882 is attached to the filling structure. The cape may drape over all or a portion of the filling structure and is fabricated from any of the materials disclosed herein. Because the cape is thin and flexible it will fit into the space between the filling structure and the aneurysm wall and will help form a blood clot which further creates a seal. The cape 882 may take any shape and may be attached to the filling structure using any of the previously described methods. FIG. 29 illustrates yet another embodiment of a filling structure with a thrombogenic material attached thereto. In FIG. 29, an annular cuff 884 is coupled with a neck region of the filling structure. The cuff 884 may be a Dacron cuff or it may be any material that is known to be thrombogenic and it is attached to the filling structure using techniques known to those of skill in the art. The cuff 844 helps form a seal by causing thrombosis in the neck region of the filling structure. A cape structure having multiple lobes 1002 may also be used to heal seal the aneurysm as shown in FIG. 33A. The lobes 1002 may be fillable or not. If fillable, as seen in FIG. 33B, the lobes have a low profile prior to filling and a larger profile after filling as seen in FIG. 33A.

Still another embodiment of a filling structure is one that is seen in FIGS. 34A-34D. In FIG. 34A, multiple filling cylinders 1006, 1008, 1009 are stacked inside one another to create a tapered or stepped filling structure as seen in FIG. 34C. FIG. 34C shows an alternative embodiment of a stacked filling structure having three cylinders 1010, 1012 and 1014. FIG. 34D shows the cylinders of FIG. 34B after they have been stacked together.

Figure 35A:
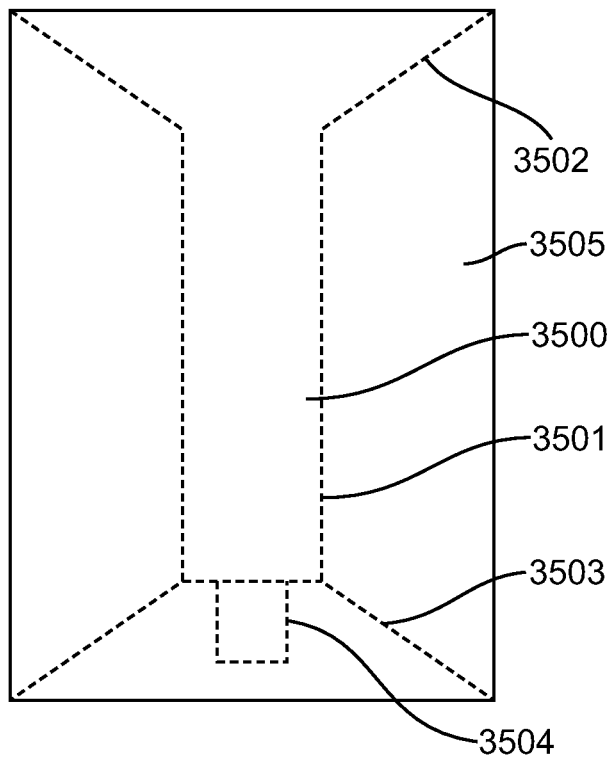
FIGS. 35A-35B illustrate an alternative embodiment of a double-walled filling structure.
Figure 35B:
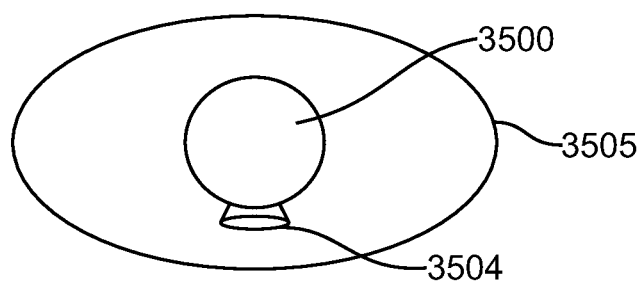

Another filling structure embodiment is seen in FIGS. 35A-35B. In FIG. 35A the inner wall of the filling structure forms lumen 3500. Lumen 3500 includes a straight tubular section 3501 and tapered portions 3502 and 3503 near the ends of the filling structure. The tapered portions 3502 and 3503 flare radially outward. Fill port 3504 is recessed into the tapered part of lumen 3503. This substantially prevents the fill port from contacting the aneurysm wall once the filling structure is filled. FIG. 35B shows an end view of the filling structure seen in FIG. 35A. In FIG. 35B, outer wall 3505 forms a round or oval shape and lumen 3500 is generally round. Additionally, outer wall 3505 is invaginated inwardly to form a convex end rim. The opposite end may also be similarly formed. Fill port 3504 is situated within the tapered part of lumen 3500. In further alternative embodiments, the fill port may be located at either end of the fill structure, or may be exposed to contact the aneurysm wall. The cross-sectional shape at each end depends on the rate of taper of the corresponding tapered portions 3502 and 3503, becoming more round as the ratio of length to width of the tapered portion increases. The filling structure may also comprise any of the sealing or other features disclosed herein, such as a tapered shoulder illustrated in FIG. 7A.

Figure 30A:
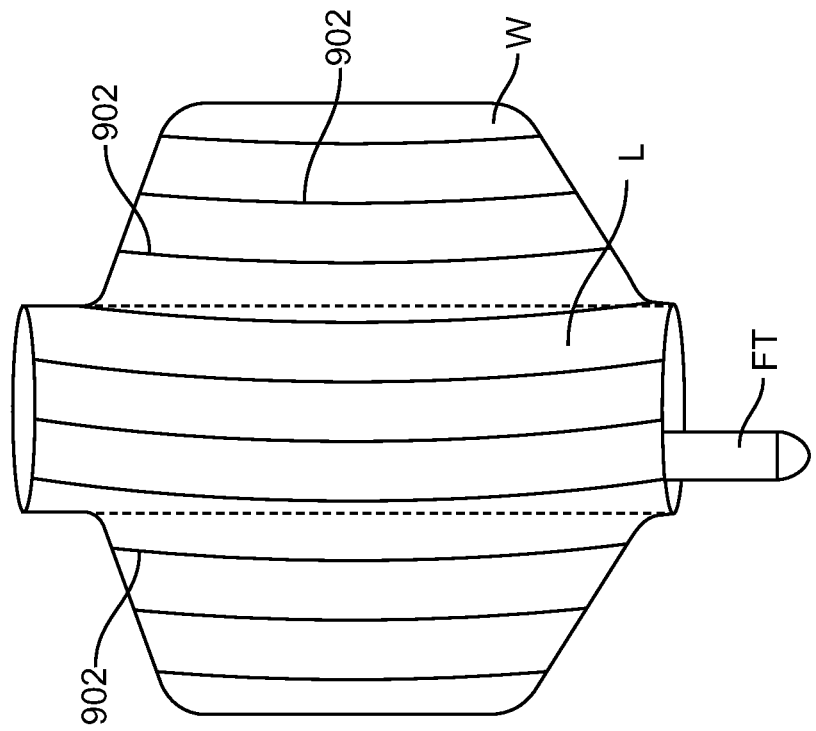
FIGS. 30A-30C illustrate several embodiments of resilient frames coupled with the filling structure.
Figure 30B:
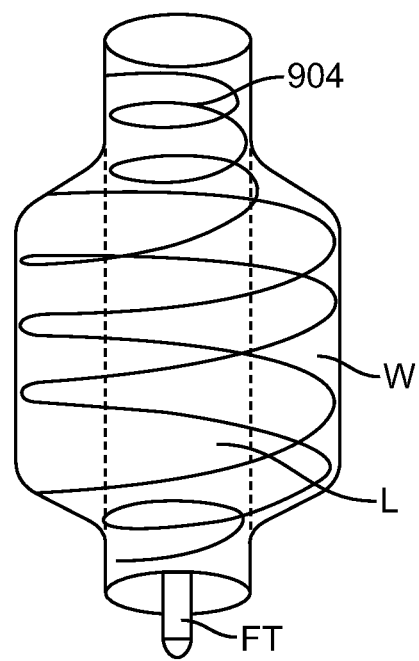
Figure 30C:
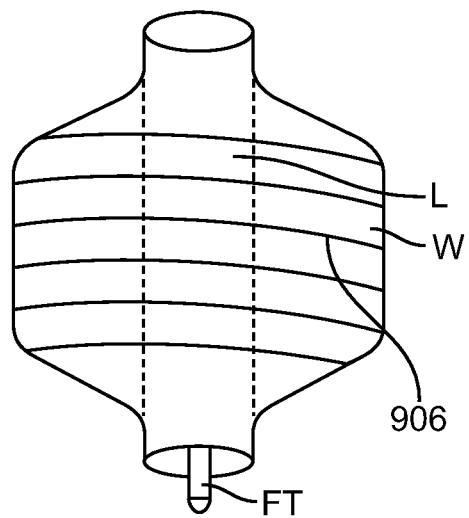

In addition to filling structures and thrombogenic materials, a resilient spring-like frame or skeleton may be used to help radially expand the filling structure into engagement with the aneurysm walls, thereby further enhancing the seal. For example, in FIG. 30A, the filling structure comprises a plurality of elongate struts 902 or ribs that are coupled with the filling structure. The struts 902 are biased to flex radially outward, therefore after a constraint is released, the struts will bow radially outward, forcing the filling structure to also expand outward. FIG. 30B illustrates another embodiment where the resilient frame comprises a helical coil 904 and FIG. 30C illustrates how the resilient frame may comprise struts which are transverse to the longitudinal axis of the filling structure. The spring-like frame may be made from any number of resilient metals such as stainless steel, nitinol or resilient polymers. The frame may be coupled to the inside or outside surface of the filling structure, or it may be embedded in between the inner and outer filling structure walls.

Figure 31A:
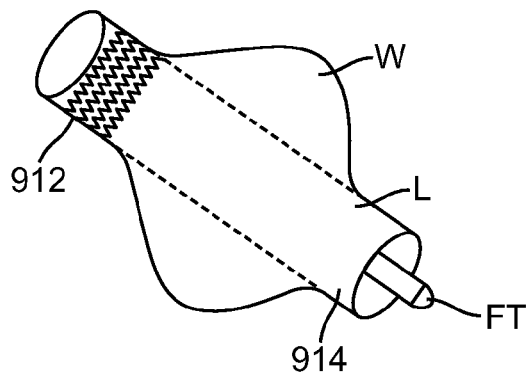
FIGS. 31A-32D illustrate various reinforced regions and patterns that may be used on a filling structure.
Figure 31B:
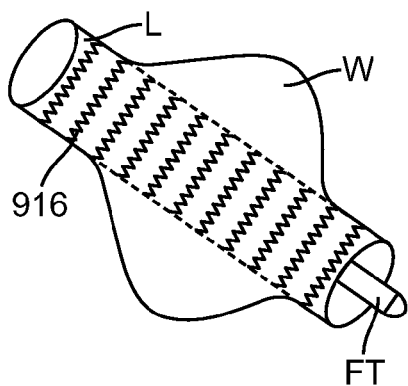
Figure 31C:
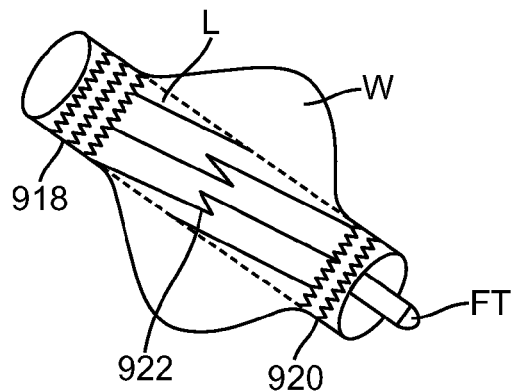
Figure 32A:
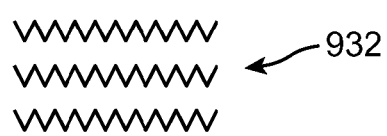
Figure 32B:
Figure 32C:
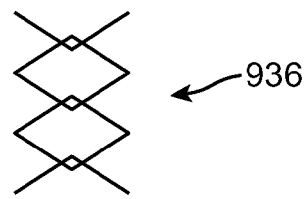
Figure 32D:
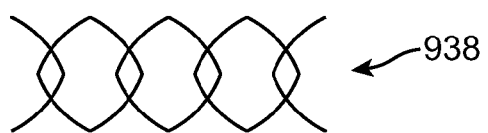

Reinforcing the ends of the filling structures may also provide a better seal since the reinforced region and/or lumen L will be rigid and cannot collapse. FIGS. 31A-31C illustrate exemplary embodiments of reinforced filling structures. In FIG. 31A, the filling structure comprises narrow neck regions 912, 914 on both ends of the main body. One of the narrow neck regions 912 is reinforced with a frame to provide additional stiffness in that region. The opposite narrow neck region 914 is shown unreinforced although it may also be reinforced. FIG. 31B illustrates reinforcement 916 along the entire filling structure longitudinal axis. FIG. 31C illustrates reinforcement on opposite ends 918, 920 of the filling structure with connector struts 922 joining both reinforced ends 918, 920. The reinforced areas may be metal, polymers or combinations thereof. Various reinforcing patterns may be used such as those well known in the stent and stent-graft arts. For example, the reinforced areas may have sine wave like patterns 932 as seen in FIG. 32A, diamond shapes 934 as in FIG. 32B, weaves 936 as in FIG. 32C or helical coils 938 as in FIG. 32D. Many other geometries may also be used.

A number of embodiments of filling structure have been disclosed. Any combination of these embodiments may also be made or substituted with one another. While use of the filling structures may have been described with respect to a two piece or a three piece endograft system, one of skill in the art will appreciate that any filling structure may be used in any endograft system. Additional features such as thrombogenic materials, thrombogenic agents, radially expanding frames and reinforced regions have also been discussed. Any of these features may also be used in combination with any of the filling structures.

A number of thrombogenic materials have also been disclosed such as polyurethanes, polycarbonates, polyesters, ePTFE, polyolefins, parylene, gelatin, silicone, etc. Any of these materials may be used as the thrombogenic material and these materials may be formed into any number of configurations such as sutures, felts, velours, weaves, knits, hydrogels, foams, embolization coils or sheets. Attachment methods include but are not limited to gluing, heat sealing, welding, sintering, suturing/sowing, electrospinning, spraying, vapor deposition or drape coating. The thrombogenic materials may be fabricated as a part of the filling structure or they may be introduced during deployment of the filling structure.

In addition to using thrombogenic materials, the surfaces of the filling structure may be modified in order to provide various material properties. For example, the surface may be textured, dimpled, etc. in order to provide a surface that helps provide the desired amount of thrombogenicity. Furthermore, the preferred embodiments have been disclosed as being composed of ePTFE with an inner layer of polyurethane. Other materials may be used as the filling structure base material and a second or third or even more layers of other materials may be coupled to the base layer in order to provide the desired material characteristics of the filling structure. Specific regions of the filling structure may also be modified with a material or drug to provide a desired effect, for example, a portion of the filling structure may be modified to be thrombogenic to help create a seal while other regions remain unmodified or modified to have a different effect. Other materials or therapeutic agents like heparin may also be applied to the surface of the tubular lumen to minimize thrombogenicity, or to promote healing and endothelialization as blood flows therethrough.

Filling materials may be any one or combination of materials that may fill the filling structure and be hardened in situ. Examples of filling materials include polyethylene glycol (PEG), silicones, etc. One of skill in the art will appreciate that any of the features disclosed herein may be substituted or combined with any of the embodiments described herein. Moreover, in this disclosure the filling structure is referred to as having an inner wall and an outer wall that may be filled and that can withstand pressures of approximately from about 30 mm Hg to about 300 mm Hg above normal systolic blood pressure. One will appreciate the filling structure may also have multiple layers. For example, as disclosed, often the filling structure comprises an ePTFE layer with a coating of polyurethane thereover. Additional layers with other materials may similarly be used in order to control the material properties such as porosity and compliance. Therapeutic agents may also be coupled to the filling structure such as a thrombogenic agent on the outside of the filling structure.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A system for treating an aneurysm, said system comprising:
at least a first double-walled filling structure having an outer wall and an inner wall, wherein the filling structure is adapted to be filled with a hardenable fluid filling medium so that the outer wall conforms to the inside surface of the aneurysm and the inner surface forms a generally tubular lumen extending from a top end of the filling structure to a bottom end of the filling structure along a first longitudinal axis to provide blood flow therethrough,
a second double-walled filling structure having an outer wall and an inner wall, wherein the second filling structure is adapted to be filled with a hardenable fluid filling medium so that the outer wall conforms to the inside surface of the aneurysm and the inner surface forms a generally tubular lumen extending from a top end of the filling structure to a bottom end of the filling structure along a second longitudinal axis to provide blood flow therethrough,
wherein each of the first and the second filling structure comprises a sealing feature, the sealing features forming a fluid seal between the filling structures and the aneurysm when the first and second filling structures are positioned side-by-side across the aneurysm with the respective top ends positioned in an upstream direction and filled with the hardenable fluid filling medium, thereby minimizing or preventing blood flow downstream of the seal and inhibiting migration of the first and second filling structures, wherein the sealing feature of the first filling structure comprises a portion having a pre-defined first and the sealing feature of the second filling structure comprises a portion having a pre-defined second shape, each of the first and second shapes comprising a vertical cross-section shape of the respective filling structure along the respective longitudinal axis when extending vertically, the vertical cross-section shape having a horizontal width dimension varying along the respective longitudinal axis, wherein the horizontal width dimension of the first pre-defined shape differs from the horizontal width dimension of the second pre-defined shape along a common horizontal axis when the first and second filling structures are aligned in parallel along the respective longitudinal axis extending vertically and the respective top ends and/or bottom ends are aligned horizontally side-by-side, wherein the second shape is complementary to the first shape when the first and second double-walled filling structures are deployed within the aneurysm, the first and second filling structures being positioned adjacent side-by-side across the aneurysm and filled with the hardenable fluid when deployed, such that engagement between the portions having the respective first and second shapes inhibit relative longitudinal movement between the first and second filling structure, wherein the first and second filling structures are separately deliverable and positionable relative to each other along the respective longitudinal axes.

2. A system as in claim 1, wherein the sealing feature of each of the first and second filling structures is disposed in a neck of the aneurysm when the filling structures are deployed within the aneurysm.

3. A system as in claim 1, wherein the sealing feature of each of the first and second filling structures is disposed upstream of the aneurysm.

4. A system as in claim 1, wherein the tubular lumen has a substantially circular cross-section perpendicular to the longitudinal cross-section.

5. A system as in claim 1, wherein the first filling structure comprises an elliptical cross-section perpendicular to the longitudinal cross-section when filled with the hardenable filling medium.

6. A system as in claim 1, wherein the first filling structure is formed by two sheets, an edge of each sheet being sealed together and adapted to withstand a filling pressure of up to 300 mm Hg above normal systolic pressure without bursting.

7. A system as in claim 1, further comprising a thrombogenic material.

8. A system as in claim 7, wherein the thrombogenic material is selected from the group consisting of polyurethane, polycarbonate, polyester, ePTFE, polyolefin, parylene, gelatin and silicone.

9. A system as in claim 7, wherein the thrombogenic material is formed into one of sutures, felts, velours, weaves, knits, hydrogels, foams, coils, sheets and combinations thereof.

10. A system as in claim 7, wherein the thrombogenic material is coupled with an outer surface of the first double-walled filling structure.

11. A system as in claim 7, wherein the thrombogenic material comprises a thrombogenic drug.

12. A system as in claim 1, wherein the inner and outer walls comprise ePTFE.

13. A system as in claim 12, wherein the inner and outer walls are at least partially covered with polyurethane.

14. A system as in claim 1, wherein the first and second shapes comprise complementary tapers that taper in opposing directions when the first and second filling structures are aligned vertically in parallel along the respective longitudinal axis and the respective top ends and/or bottom ends aligned horizontally side-by-side.

15. A system as in claim 1, wherein each of the first shape and second shape varies in width along the first and second longitudinal axes, respectively.

16. A system as in claim 1, wherein each of the first shape and second shape varies in width by variation in a distance between the outer wall and the respective longitudinal axis.

17. A system as in claim 14, wherein the first shape and second shape taper in opposite directions such that engagement between the outer walls of the first and second filling structure along the complementary tapers inhibit relative movement between the first and second filling structures along their respective longitudinal axis.

18. A system as in claim 16, wherein the portion of the first filling structure having the first shape includes substantially the entire first filling structure along the first longitudinal axis and the portion of the second filling structure having the second shape includes substantially the entire second filling structure along the second longitudinal axis.

19. The system of claim 1, wherein the respective horizontal widths differ along a common horizontal axis along a substantial part of the portions having the respective first and second sealing features when the first and second filling structures are aligned vertically in parallel along the respective longitudinal axis with the respective top ends and/or bottom ends aligned horizontally side-by-side.

20. The system of claim 1, wherein the respective horizontal widths differ along the common horizontal axis along substantially the entire portions having the respective first and second sealing features when the first and second filling structures are aligned vertically in parallel along the respective longitudinal axis with the respective top ends and/or bottom ends aligned horizontally side-by-side.

21. A system for treating an aneurysm, said system comprising:

at least a first double-walled filling structure having an outer wall and an inner wall, wherein the filling structure is adapted to be filled with a hardenable fluid filling medium so that the outer wall conforms to the inside surface of the aneurysm and the inner surface forms a generally tubular lumen extending from a top end of the filling structure to a bottom end of the filling structure along a first longitudinal axis to provide blood flow therethrough, a second double-walled filling structure having an outer wall and an inner wall, wherein the second filling structure is adapted to be filled with a hardenable fluid filling medium so that the outer wall conforms to the inside surface of the aneurysm and the inner surface forms a generally tubular lumen extending from a top end of the filling structure to a bottom end of the filling structure along a second longitudinal axis to provide blood flow therethrough, wherein each of the first and the second filling structure comprises a sealing feature, the sealing features forming a fluid seal between the filling structures and the aneurysm when the first and second filling structures are positioned side-by-side across the aneurysm with the respective top ends positioned in an upstream direction and filled with the hardenable fluid filling medium, thereby minimizing or preventing blood flow downstream of the seal and inhibiting migration of the first and second filling structures, wherein the sealing feature of the first filling structure comprises a portion having a pre-defined first shape and the sealing feature of the second filling structure comprises a portion having a pre-defined second shape, wherein the first and second shapes are adapted such that, when each of the first and second filling structures are expanded to full capacity and aligned in parallel along their respective longitudinal axes extending vertically and the respective top ends and/or bottom ends are aligned side-by-side horizontally, the portion having the first pre-defined shape comprises an upwards facing surface and the portion having the second-predefined shape comprises a downwards facing surface along a common horizontal plane such that, when the respective filling structures are deployed adjacent and side-by-side across the aneurysm, engagement between the upwards facing surface and the downwards facing surface facilitates sealing and inhibits longitudinal movement between the first and second filling structures, wherein the first and second filling structures are separately deliverable and positionable relative to each other along the respective longitudinal axes.

22. A system as in claim 1, wherein each of the complementary shapes of the first and second filling structures has a horizontal cross-section that is symmetrical about the respective longitudinal axis.

\* \* \* \* \*